US006287869B1

United States Patent
Hug et al.

(12)

(10) Patent No.: US 6,287,869 B1
(45) Date of Patent: Sep. 11, 2001

(54) ANALYTICAL INSTRUMENT USING A SPUTTERING METAL ION LASER

(76) Inventors: William F. Hug, 2239 Paloma St., Pasadena, CA (US) 91104; Ray D. Reid, 921 Englewild St., Glendora, CA (US) 91741

(*) Notice: Subject to any disclaimer, the term of this patent is extended or adjusted under 35 U.S.C. 154(b) by 0 days.

(21) Appl. No.: 09/250,820

(22) Filed: Feb. 17, 1999

(51) Int. Cl.[7] .................................................. G01N 21/00

(52) U.S. Cl. ...................... 436/164; 436/172; 422/82.05; 422/82.09

(58) Field of Search ............................... 436/161, 164, 436/172; 422/82.05, 82.09

(56) References Cited

U.S. PATENT DOCUMENTS

| 3,646,476 | * | 2/1972 | Barker et al. ................. 331/94.5 |
|---|---|---|---|
| 3,891,943 | * | 6/1975 | Dowley et al. ............... 331/94.5 G |
| 4,085,385 | * | 4/1978 | Fein et al. ..................... 331/94.5 D |
| 4,641,313 | | 2/1987 | Tobin et al. ..................... 372/56 |
| 4,730,334 | * | 3/1988 | Collins et al. .................... 372/88 |
| 4,953,176 | | 8/1990 | Ekstrand ......................... 372/107 |
| 5,088,820 | * | 2/1992 | Winefordner et al. ........... 356/301 |
| 5,311,529 | | 5/1994 | Hug ................................... 372/35 |

OTHER PUBLICATIONS

Cho, N., Song, S., and S.A. Asher, "UV Resonance Raman and Excited–State Relaxation Rate Studies of Hemoglobin", Biochemistry, vol. 33, (1994): pp. 5932–5941.

Cho, N., and S.A. Asher, "UV Resonance Raman and Absorption Studies of Angiotensin II Conformation in Lipid Environments", Biospectroscopy, vol. 2, (1996): pp. 71–82.

Asher, S.A., "UV Resonance Raman Spectroscopy for Analytical, Physical, and Biophysical Chemistry, Part 1", Anal. Chem., vol. 65, No. 2, (Jan. 15, 1993): pp. 59–66.

McNeil, et al., "Ultraviolet Laser Action From Cu II in the 2500–A Region", Appl. Phys. Letters, vol. 28, No. 4, (Feb. 15, 1976): pp. 207–209.

Warner, et al., "Metal–Vapor Production by Sputtering in a Hollow–Cathode Discharge: Theory and Experiment", J. App. Phys., vol. 50, No 9, (Sep. 1979): pp. 5694–5703.

Gerstenberger, et al., "Hollow Cathode Metal Ion Lasers", IEEE J. Quantum Elect., vol. QE–16, No. 8, (Aug. 1980): pp. 820–834.

Solanki, et al., "Multiwatt Operation of Cu II and Ag II Hollow Cathode Lasers", IEEE J. Quant. Elect., vol. QE–16, No. 12, (Dec. 1980): pp. 1292–1294.

(List continued on next page.)

*Primary Examiner*—Jeffrey Snay
(74) *Attorney, Agent, or Firm*—Dennis R. Smalley

(57) ABSTRACT

Internal mirror sputtering metal ion lasers are disclosed which employ laser mirrors and a resonator internal to and integral with the laser plasma tube. Preferred lasers use silver, copper, gold and other metals individually or in combination as optically active materials and buffer gases of helium, neon, argon and other noble gases. Laser mirrors are utilized to enhance or reject selected combinations of emission wavelengths. Because of the rapid response time of these lasers, they may be employed as quasi-CW devices with laser output pulse widths ranging from a few microseconds to hundreds of microseconds and with very low input power ranging from a few watts to about 500 watts. The disclosed lasers approach the size, weight, power consumption, and cost of a helium-neon laser while providing quasi-continuous output up to hundreds of milliwatts at a wide range of wavelengths from about 200 nm in the deep ultraviolet to about 2000 nm in the middle infrared. The disclosed lasers employ methods for reduction of arc formation, and use of commutated power supplies which reduce arc formation and extend the lifetime of the lasers. Applications for these lasers include analytical instruments such as Raman spectrometers, high-pressure liquid chromatography systems, and plane or gel electrophoresis systems.

27 Claims, 11 Drawing Sheets

OTHER PUBLICATIONS

Asher, S.A., "Resonance Raman Spectroscopy of Hemoglobin", Methods in Enzymology, vol. 76, (1981): pp. 371–413.

Asher, S.A., et al., "Development of a New UV Resonance Raman Spectrometer for the 217–400–nm Spectral Region", Rev. Sci. Instr. vol. 54, (Dec. 1983): pp. 1657–1662.

Asher, S.A., "UV Resonance Raman Studies of Molecular Structure and Dynamics: Applications in Physical and Biophysical Chemistry", Ann. Rev. Phys. Chem., vol. 39, (1988): pp. 537–588.

Milofsky, R. E., et al., "Native Fluorescence Detection of Nucleic Acids and DNA Restriction Fragments in Capillary Electrophoresis", Anal. Chem., vol. 65, (Jan. 1993): pp. 153–157.

Asher, S.A., "UV Resonance Raman Spectroscopy for Analytical, Physical, and Biophysical Chemistry, Part 2", Anal. Chem., vol. 65, No. 4, (Feb. 15, 1993): pp. 201–210.

Arslanbekov, et al., "Self–consistent Model of High Current Density Segmented Hollow Cathode Discharges", J. App. Phys., vol. 81, No. 2, (Jan. 1997): pp. 1–15.

Chi, Z., et al., "UV Resonance Raman–Selective Amide Vibrational Enhancement: Quantitative Methodology for Determining Protein Secondary Structure", Biochemistry, vol. 37, (1998): pp. 2854–2864.

* cited by examiner

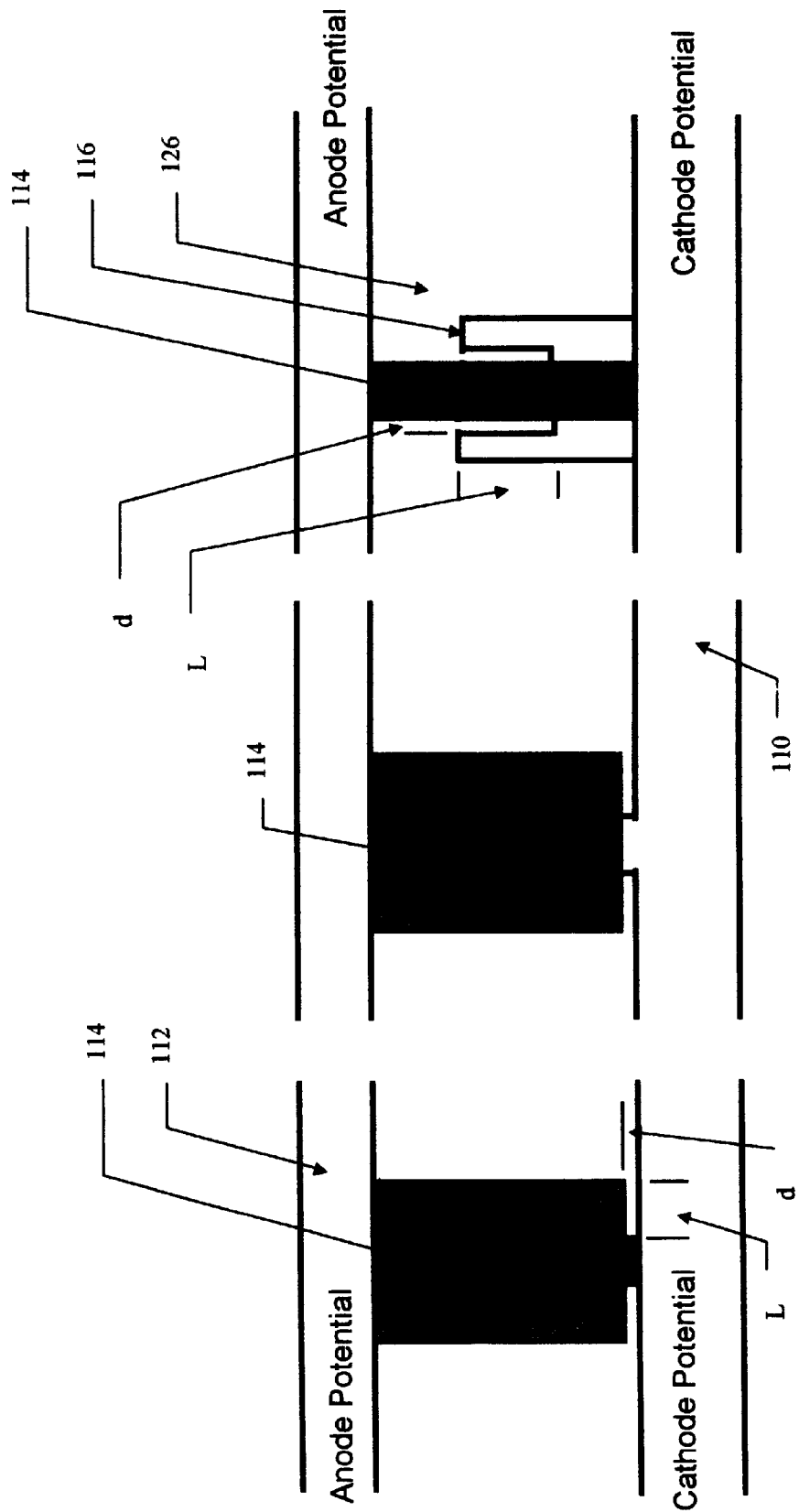

ANALYTICAL INSTRUMENT USING A SPUTTERING METAL ION LASER

FIELD OF THE INVENTION

The field of the present invention is analytic instruments using lasers for supplying incident radiation to an unknown sample, and more particularly analytic instruments using sputtering metal ion lasers.

BACKGROUND OF THE INVENTION

The background for and disclosure of the invention are explained with reference to the following patents and publications each of which is hereby incorporated by reference as if set forth in full herein:
(1) Milofsky, R. E. and E. S. Yeung, "Native Fluorescence Detection of Nucleic Acids and DNA Restriction Fragments in Capillary Electrophoresis", *Anal. Chem.*, vol. 65, (1993): pp. 153–157;
(2) Chi, Z., X. G. Chen, J. S. W. Holtz and S. A. Asher, "UV Resonance Raman-Selective Amide Vibrational Enhancement: Quantitative Methodology for Determining Protein Secondary Structure", *Biochemistry*, Vol. 37, (1988): pp. 2854–2864;
(3) Thomas, G. J., *Spectroscopy of Biological Systems*, Ed. Clark, R. J. and R. E. Hester, John Wiley (1986);
(4) Cho, N., Song, S., and S. A. Asher, "UV Resonance Raman and Excited-State Relaxation Rate Studies of Hemoglobin", *Biochemistry*, Vol. 33, (1994): pp. 5932–5941;
(5) Cho, N., and S. A. Asher, "UV Resonance Raman and Absorption Studies of Angiotensin II Conformation in Lipid Environments", *Biospectroscopy*, Vol. 2, (1996): pp. 71–82;
(6) Chronister, E. L., Corcoran, R. C. Song, L., and El-Sayed, M., *Proc. Nat'l Acad. Sci.* (USA), Vol. 83, (1986): pp. 8580–8583;
(7) Barry, B., and R. A. Mathies, *Biochemistry*, Vol. 26, (1987): pp. 59–64;
(8) Asher, S. A., *Methods in Enzuymology*, Vol 76, (1981): pp. 371–383;
(9) Spiro, R. G., *Biological Applications of Raman Spectroscopy*: Vol II, John Wiley (1987);
(10) Asher, S. A.,*Ann. Rev. Phys. Chem.*, Vol. 39, (1988): pp. 537–542;
(11) Asher, S. A., Johnson, C. R. and J. Murtaugh, Rev. Sci. Instr. Vol. 54, (1983): pp. 1657–1659;
(12) Asher, S. A., *Anal. Chem.*, Vol. 65, No.4, (Feb.15, 1993): pp. 201–210.
(13) Gerstenberger, et al., "Hollow Cathode Metal Ion Lasers", *IEEE J. Quantum Elect.*, vol. QE-16, No. 8, (August 1980): pp. 820–834;
(14) U.S. Pat. No. 4,641,313, entitled "Room Temperature Metal Vapour Laser", to Tobin;
(15) McNeil, et al., "Ultraviolet Laser Action From Cu ll in the 2500-A Region", *App. Phys. Letters*, vol. 28, No.4, (Feb. 15, 1976): pp. 207–209;
(16) Warner, et al., "Metal-Vapor Production by Sputtering in a Hollow-Cathode Discharge: Theory and Experiment", *J. App. Phys.*, vol. 50, No 9, (September 1979): pp. 5694–5703;
(17) Solanki, et al., "Multiwatt Operation of Cull and Agll Hollow Cathode Lasers", *IEEE J. Quant Elect*, vol. QE-16, No.12, (December 1980): pp. 1292–1294.
(18) Arslanbekov, et al., "Self-consistent Model of High Current Density Segmented Hollow Cathode Discharges",*J. App. Phys.*, vol. 81, No 2, (January 1997): pp. 1–7;
(19) U.S. Pat. No. 5,311,529, entitled "Liquid Stabilized Internal Mirror Lasers", to Hug; and
(20) U.S. Pat. No. 4,953,176, entitled "Angular Optical Cavity Alignment Adjustment Utilizing Variable Distribution Cooling", to Ekstrand.

Existing lasers which emit in the deep ultraviolet between 200 nm and 300 nm have serious limitations in one or more of the following: (1) the selection of emission wavelengths, (2) average or instantaneous output power, (3) power consumption, (4) reliability, (5) size, (6) weight, and (7) cost. Because laser sources without these limitations have never been developed and commercialized, a wide range of commercial analytical instrumentation that could benefit from such sources have never been enabled.

Capillary electrophoresis, high performance liquid chromatography, laser-induced fluorescence, fluorescence microscopy, and Raman spectroscopy are emerging as powerful analytical tools for a wide range of biological and chemical research. In addition, these instrumental techniques are being increasing used in commercial applications such as product inspection during the manufacture of pharmaceutical and medical products, manufactured food products and other chemical products.

Capillary electrophoresis (CE) allows rapid separation of complex chemical and biochemical mixtures. Laser induced fluorescence (LIF) allows the sensitive detection of analytes. Raman spectroscopy (RS) allows a high level of chemical specificity. The sensitivity and selectivity of these analytical instruments are today considerably enhanced when combined with a laser, which emits in the deep UV between 200 nm and 300 nm. The principle limitation to widespread commercial use of these systems is lack of commercially suitable UV lasers, particularly associated with limitations in emission wavelengths, duty cycle, size, power consumption, complexity, cost and reliability of existing lasers. A need exists in these fields for improved laser systems, particularly in the deep UV, that overcome these disadvantages either singly or in combination.

Capillary electrophoresis continues to evolve as a powerful analytical method for separation and analysis of complex chemical analytes. A major direction of development in CE is toward smaller capillaries, allowing faster separations. As capillary diameters decrease below 50 microns and head toward 20 or even 10 microns, the problem of providing enough light to excite fluorescence in a sample being examined determines the detection limit. This is discussed in reference (1) by Milofsky and Yeung, 1993. When capillary diameters were larger, deuterium lamps were employed to excite native fluorescence in biomolecules. However, as capillary diameters decrease, deuterium lamps no longer have sufficient source radiance at the desirable deep UV wavelengths to enable them to be employed. Lasers have been recognized as the solution to this problem. However, because lasers of reasonable cost and size only emit in the visible or near IR, fluorescent dye derivatization techniques were developed to enable the use of these lasers for detection. Derivatization with fluorescent labels limits the types of molecules which can be studied, reduces CE's ability to find unexpected analytes in complex systems, may perturb the very cellular chemistry being studied, and can reduce overall sensitivity. A sensitive native CE/LIF detection method for nucleic acids and DNA restriction fragments has already been demonstrated as described in reference (1) by Milofsky and Yeung in 1993. Both the 275.4 nm line of an argon ion laser and the 248 nm line from a waveguide KrF laser were able to excite native fluorescence in the nucleic acids with a few mW of laser power. Detection limits for guanosine and adenosine monophosphate of $1.5 \times 10^{-8}$ and $5 \times 10^{-8}$ M, respectively, were as much as three orders of magnitude lower than UV fluorescent tag detection. However, the complexity and cost of the laser employed severely restrict the general utility of this technique. A need exists in this field for improved laser systems with reduced complexity and/or cost to make practical the above noted applications.

Raman spectroscopy has been demonstrated as a uniquely important technique for analyzing biological structure and function. Traditional Raman spectroscopy has been used to study a wide range of biological molecules such as protein secondary structure, nucleic acid folding and membrane phase transitions as described in reference (2) by Chi, et al., 1988. Most of this work has examined purified chemical systems, such as polymers, proteins, and nucleic acid systems, but a number of studies have probed complicated systems such as industrial and environmental samples, as well as DNA structure in whole viruses as described in reference (3) by Thomas, 1986.

The aromatic ring structures of tyrosine, tryptophane, and phenylalanine offer excellent LIF and UV resonance Raman (UVRR) cross-sections. The abundance of these three targets in the vast majority of proteins has made possible such investigations as the determination of protein acid denaturation using UVRR, characterization of excited-state relaxation rates in hemoglobin as described in reference (4) by Cho, et al., 1994, and elucidation of the secondary structure of angiotensin II as described in reference (5) by Cho, et al., 1996.

Resonance Raman excitation results in scattering cross-sections that are enhanced by as much as eight orders of magnitude over normal Raman spectroscopy. Resonance Raman sensitivity is comparable to that of fluorescence. Selectivity can be greater than fluorescence because Raman spectra have higher information content. Narrow Raman emission bands carry a great deal more information on molecular structure, in contrast to broadband fluorescence emission. It also allows selective study of specific chromophoric segments of a macromolecule. Visible wavelength resonance Raman spectroscopy has been uniquely incisive in the development of the understanding of energy transduction in rhodopsin and bacteriorhodopsin as described in reference (6) by Chronister, et al., 1986 and in reference (7) by Barry et al., 1987. It has also been incisive in structural and dynamical studies of numerous heme proteins such as hemoglobin and cytochrome oxidase as described in reference (8) by Asher, 1981 and in reference (9) by Spiro, 1987. However, detection of the Raman signal is usually complicated by the presence of background fluorescence from not only the molecules of interest but also from solvents and impurities.

More than ten years ago, instrumentation was developed which allowed excitation in the UV absorbing bands of molecules as described in references (10) by Asher, 1988 and in reference (11) by Asher et al., 1983. These fundamental studies have shown that unique information is available from UV resonance Raman studies of macromolecular structure. In addition, it has been shown that the ubiquitous fluorescence, which is a major impediment for visible wavelength Raman studies, does not occur for UV spectral studies below 260 nm. This is because at these high energies the excited state of most molecules in a condensed phase relaxes by means of fast radiationless processes before it has time to fluoresce as described in reference (12) by Asher, 1993.

As described above, deep UV laser radiation is useful for a wide range of commercially valuable applications. A key feature impeding the commercial development of these applications is the lack of availability of a deep UV laser of suitable cost, size, weight, power consumption and optical output properties. Thus, a need exists in these arts for a laser device that fulfills one or more of these deficiencies.

Metal ions such as those of copper, silver, and gold can provide a rich array of possible laser emission wavelengths as described in reference (13) by Gerstenberger, 1980. The historical difficulty in developing useful metal ion lasers has been associated with the method of generating an adequate metal vapor density within the gain region of the laser. Direct vaporization by evaporation or sublimation requires very high temperatures, typically about 1500° C. for copper. Operation of lasers at these temperatures requires very high power consumption and is a major source of unreliability. In addition, in positive column discharge configurations of these lasers, insufficient population of high-energy states of copper or gold is developed to enable output at the deep ultraviolet emission lines.

A method of providing adequate metal vapor densities at lower operating temperature is through the use of volatile compounds of the metal such as a metal halide as described in reference (14) by Tobin. These types of metal ion lasers still require substantial heating of the volatile metal compound, to temperatures near 300° C. instead of 1500° C. However, in addition, there is a further limitation of these lasers due to the limited range of metals that can be combined into these suitable compounds. A further limitation of these lasers is that the self-terminating transitions described by Tobin only operate with very short pulse widths, making them undesirable for many biological applications.

One way to avoid these limitations is by the use of sputtering to achieve the desired metal ion densities. Sputtering metal ion hollow cathode lasers have been demonstrated in several laboratories starting about 1976, as described in reference (15) by McNeil, (16) by Warner, (17) by Solanki and up to the present time as described in reference (18) by Arslanbekov, et al., 1997. An advantage of the sputtering method of providing metal vapor is that this can be done at room temperature, thus avoiding the power requirements and warm-up time associated with the other metal vapor lasers noted above. These lasers have demonstrated the ability to provide emission over a wide range of wavelengths from about 200 nm in the deep UV to nearly 2000 nm in the middle infrared. Threshold for lasing varies considerably from laser line to laser line, but typically ranges from about 2A to 40A at 250V to 500V. Thus the input power to achieve threshold varies from about 500W to 10,000W.

Sputtering metal ion hollow cathode lasers described in the literature have several problems that limited their commercial use. These limitations are summarized as: too costly to manufacture both the laser plasma tube and power supply, too large, too fragile, poor lifetime and overall reliability, limited variety of laser emission lines, and limited variety of laser output performance characteristics.

Hollow cathode sputtering metal ion lasers used laser plasma tubes that were sealed on each end either with Brewster angle windows or laser mirrors. For tubes sealed with Brewster angle windows, the laser mirrors were mounted external to the laser tube. When laser mirrors were used to seal the ends of the laser tube, the critical reflecting surfaces of the mirrors were internal to the hermetic envelope of the laser plasma tube. In both cases, the structure used to maintain laser mirrors in alignment with respect to each other and with respect to the laser tube was external to the laser tube. This external structure is referred to as the external resonator structure.

In addition prior hollow cathode sputtering metal ion lasers utilized bulky, expensive, unreliable, and fragile designs for cathodes, cathode supports, and other tube design elements which made these lasers susceptible to arcing, gas clean up, and other failure mechanisms within the laser. Laser tubes of the prior art used epoxy to seal Brewster windows or mirrors. Power supplies used with these lasers were bulky, expensive, and employed designs which were not compatible with suppression of arcing within the laser tube.

For the reasons noted above, and in particular for use in the applications noted above, a need exists for lasers having one or more of reduced size, reduced weight, reduced power consumption, less restrictive cooing requirements, increased reliability, decreased cost of manufacture, and/or operation in combination with appropriate output wavelengths, appropriate instantaneous output power, and appropriate average output power.

SUMMARY OF THE INVENTION

It is a first objective of this invention to provide a sputtering metal ion hollow cathode laser for use in analytical instrumentation.

It is a second objective of the invention to create a sputtering metal ion hollow cathode laser which has low power consumption, preferably less than 500 hundred watts.

It is a third objective of this invention to create a sputtering metal ion hollow cathode laser that is compact and lightweight, preferably nearly as compact and lightweight (e.g. no more than twice the size or weight) and more preferably as compact and lightweight, and most preferably more compact and of lighter weight than a 25 milliwatt helium-neon laser.

It is a fourth objective of this invention to create a sputtering metal ion hollow cathode laser that is preferably nearly as inexpensive (e.g. no more than twice the price), and more preferably as inexpensive and most preferably less expensive than a 25 milliwatt helium-neon laser.

It is a fifth objective of the invention to create a sputtering metal ion hollow cathode laser that can emit at one or more simultaneous wavelengths in the deep ultraviolet between about 200 nm and 300 nm.

It is a sixth objective of the invention to provide a sputtering metal ion hollow cathode laser with enhanced ruggedness and dependability, preferably as rugged and dependable, and most preferably more rugged and dependable than a 25 milliwatt helium-neon laser.

It is a seventh objective of this invention to create a sputtering metal ion hollow cathode laser that emits in the near infrared between about 700 nm and about 2000 nm, and more preferably between about 700 nm and about 900 nm.

A first aspect of the invention provides an analytical instrument which includes (a) a holder for holding a sample to be analyzed; (b) a source of radiation producing a narrow band of wavelengths; (c) at least one element for causing the radiation to be incident on the sample; and (d) a detection system for detecting selected radiation resulting from interaction between the incident radiation and the sample. The source of radiation includes (1) a hollow cathode having an inner surface at least partially surrounding an opening; (2) an anode spaced from the cathode; (3) a hermetic envelope enclosing a buffer gas and the opening; (4) a first mirror having a high reflective surface, wherein the high reflective surface is at least partially within the hermetic envelope; (5) a second mirror having a partially transmitting surface, wherein the partially transmitting surface is at least partially within the hermetic envelope; (6) an optical axis defined by the first mirror and second mirror and extending through the opening; and (7) a source of electric power connected to the anode and cathode for forming an optical gain medium within the opening.

A second aspect of the invention provides a sputtering metal ion hollow cathode laser system for use in an analytic instrument that analyzes chemical composition or structure of a sample. The system includes a radiation source as noted above in association with the first aspect of the invention. The beam produced by the radiation source is used in the analytic instrument.

A third aspect of the invention provides a sputtering metal ion hollow cathode laser system similar to the radiation source as noted above in association with the first aspect of the invention. Additionally the optical axis is fixed and maintained in position by the hermetic envelope.

A fourth aspect of the invention provides a sputtering metal ion hollow cathode laser system similar to the radiation source as noted above in association with the first aspect of the invention. Additionally, the first mirror and second mirrors are bonded to the envelope using a substantially non-permeable sealing material.

A fifth aspect of the invention provides a sputtering metal ion hollow cathode laser system similar to the radiation source as noted above in association with the first aspect of the invention with the addition of the inner surface of the hollow cathode including at least two different metals.

A sixth aspect of the invention provides a sputtering metal ion hollow cathode laser system similar to the radiation source as noted above in association with the first aspect of the invention. Additionally, the electric potential provides the cathode with a cathode potential and the anode with an anode potential. Additionally, at least one dielectric material has a surface which is in the hermetic envelope and separates at least one conducting surface at the cathode potential from at least one conducting surface at the anode potential. Furthermore, a contact region between the surface of the at least one dielectric and a partially opposing surface of the at least one conducting surface at the cathode potential is located at an end of an undercut region.

A seventh aspect of the invention provides a sputtering metal ion hollow cathode laser system similar to the radiation source as noted above in association with the first aspect of the invention. Additionally, at least one of the first mirror and second mirror are provided with a coating that enhances emission of the at least one desired wavelength or suppresses emission of at least one undesired wavelength.

An eighth aspect of the invention provides a sputtering metal ion hollow cathode laser system similar to the radiation source as noted above in association with the first aspect of the invention. Additionally, the source of electric power provides modulated electric power to the cathode and anode such that part of the time an optical gain of the laser is above a lasing threshold and such that part of the time the optical gain of the laser is below the threshold.

Additional aspects of the invention provide methods of producing laser radiation that are counterparts to the system aspects noted above. Further aspects of the invention provide methods of using the produced laser radiation.

Further objectives and aspects of the invention will be apparent to those of skill in the art upon review of the detailed description of embodiments to follow. Finally it is an objective of the invention to achieve the above noted objectives alone or in combination and to provide the above noted aspects alone or in combination.

BRIEF DESCRIPTION OF THE DRAWINGS

The invention can be further understood from the following figures in conjunction with the preferred embodiments to be discussed hereafter.

FIG. 3a depicts contact between an insulating material and a conducting surface at the cathode potential where an undercut is provided in the insulating material.

FIG. 3b depicts contact between an insulating material and a conducting surface at the cathode potential where an undercut is provided in the conducting material.

FIG. 3c depicts contact between an insulating material and a conducting surface at the cathode potential where an undercut is provided by sandwiching the insulating material between supplemental conducting elements which are at the cathode potential.

DETAILED DESCRIPTION OF PREFERRED EMBODIMENTS

To address the limitations and problems in the art noted above, this patent discloses a number of enhancements associated with the use of sputtering metal ion hollow cathode (SMIHC) lasers including but not limited to: (1) use of internal mirror/internal resonator laser plasma tube design to improve ruggedness, to improve reliability, and/or to reduce cost, (2) committing the input power to reduce average input power and/or to reduce cost while providing for laser emission at a variety wavelengths (e.g. from the deep UV to mid IR wavelengths), and/or to provide extended lifetime, (3) cathode mounting and support techniques which allow for improved lifetime, provide for ruggedness, reliability, and/or low cost, (4) geometry for low cost, and (5) hermetic sealing of laser mirrors to improve shelf life and/or operating life. Improved SMIHC lasers may incorporate these enhancements alone or in various combinations.

Figure 1A:
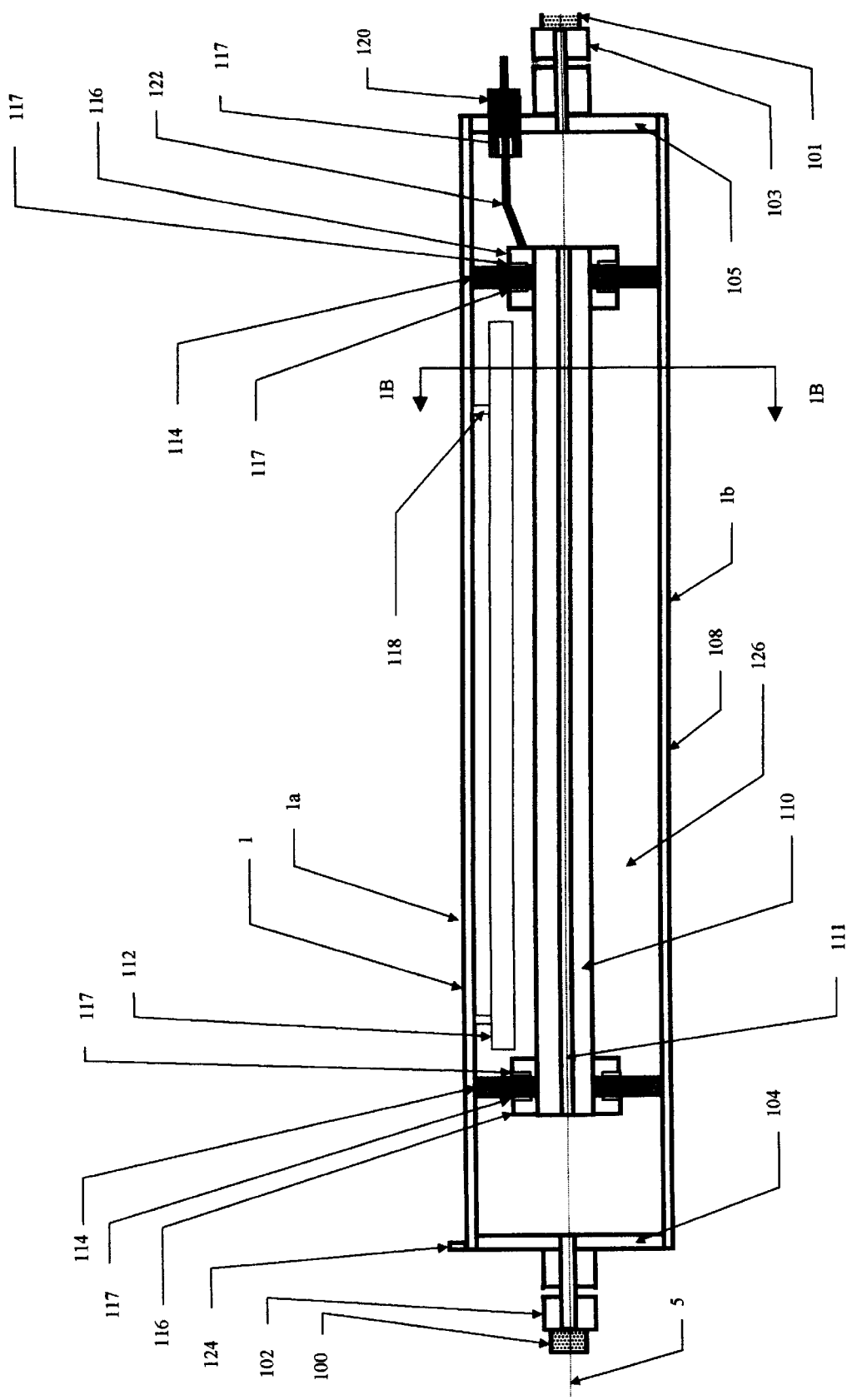
FIG. 1a depicts a longitudinal cross-sectional view of an internal mirror/internal resonator hollow cathode sputtering metal ion laser.
Figure 1B:
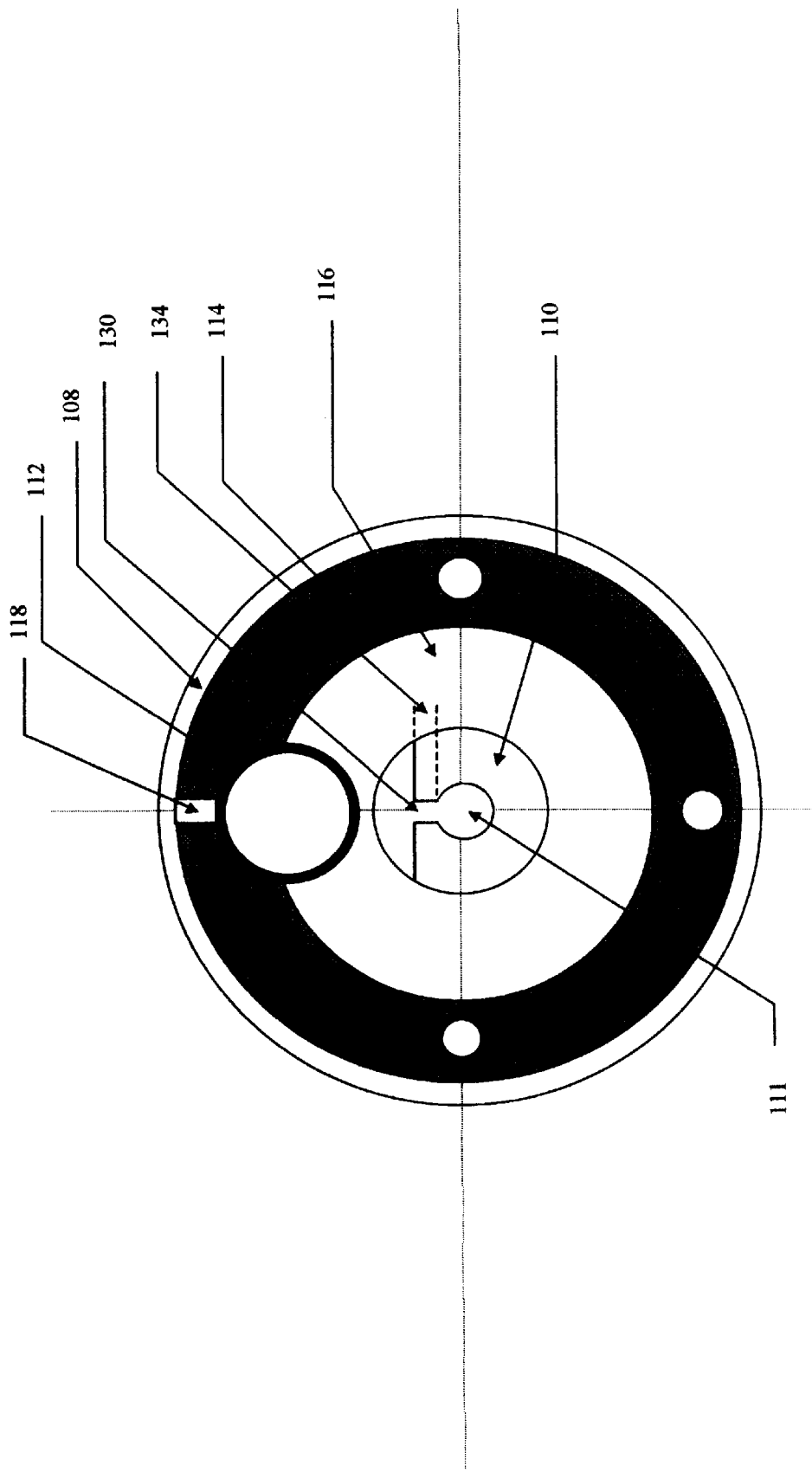
FIG. 1b depicts a cross-sectional view of the laser of FIG. 1a along lines 1b—1b.

The laser tube of the first preferred embodiment is depicted in FIGS. 1a and 1b wherein a hollow cathode sputtering metal-ion laser plasma tube with internal mirrors and internal resonator is illustrated. FIG. 1a shows the laser plasma tube in longitudinal cross-section, where FIG. 1b shows it in lateral cross-section. Referring to FIG. 1a, the hermetic laser plasma tube assembly 1 includes a high reflecting laser mirror 101 and partially transmitting laser mirror 100 disposed at opposite ends of the hermetic assembly and hermetically bonded to adjustment mechanisms 102 and 103 for sealing and aligning the laser mirrors, hermetic end caps 104 and 105 at opposite ends of the hermetic assembly, a thermally and electrically conducting hermetic envelope 108, a hollow cathode 110, with opening 111, an anode 112, dielectric cathode supports 114, conducting cathode interface supports 116 with arc suppression gaps 117 in conjunction with the dielectric cathode supports 114, conducting anode supports 118, dielectric hermetic cathode electrical feedthru 120 with arc suppression gap 117, conducting wire connecting cathode to feedthru 122, anode electrical connection 124, and buffer gas 126.

As indicated in FIG. 1a the cathode is preferably elongated (i.e. its length is longer than the cross-sectional dimension of the opening in the cathode). More specifically it is preferred that the ratio of cathode length to cross-sectional dimension of the opening in the cathode is greater than three, more preferably greater than thirty, and most preferably greater than one hundred. It is also preferred that the opening extend along the length of the cathode. However, it is conceivable in some embodiments the opening would not extend the entire length of the cathode but instead one or more mirrors could would be placed in the opening to redirect the optical path away from the closed end or ends of the cathode.

In the example of FIGS. 1a and 1b the interior of the cathode (i.e. the surface surrounding the opening) has access to the anode along a slot in a side of the cathode. The slot and the anode typically have similar lengths. The slot has sufficient width to allow effective set up of a glow discharge in the cathode opening. In alternative embodiments the slot and opening may extend different lengths or a slot may not be used at all. In stead of a slot, for example, the cathode might be perforated with a large number of holes each of sufficient size to allow an effective glow discharge to be established within the opening in the cathode. The holes may be of circular shape or be of an elongated shape (e.g. oval or rectangular). It is preferred that the holes are circular and that there be at least two holes per inch along the effective length of the cathode (i.e. the portion of the cathode that can contribute to the glow discharge), and more preferably more than five holes per inch.

In the embodiment depicted in FIG. 1a, the anode is external to the opening in the cathode. In other preferred embodiments, the anode may be located inside the opening in the cathode, the cathode may be inside the anode, multiple anodes and cathode may be positioned to surround a gain region, and/or the cathode and anode may reverse polarity when driven by an AC potential.

In the example of FIG. 1a the cathode is located completely within the hermetic envelope. In alternative embodiments the cathode may be only partially within the hermetic envelope. The outer surface of the cathode may form part of the hermetic envelope.

The hermetic envelope materials of the laser plasma tube 1, and especially 108, 104, and 105 may be of importance to the performance of the laser. These hermetic envelope elements support the alignment of the laser mirrors 100, 101 relative to each other and to the gain material generated within the opening 111 in the hollow cathode 110. Misalignments of the relative orientation of these laser plasma tube elements may cause the laser output to vary and beam axis position and mode properties to change. In practical operation of a laser plasma tube, temperature gradients around and along the hermetic envelope are generated due to temperature differences between the envelope and the surrounding ambient environment. The higher the input power per unit length, the higher the average envelope temperature and the worse the asymmetrical temperature distribution problem. The asymmetry in temperature distribution is due to gravitational convection around the laser tube. As the input power per unit length or volume of the laser tube is increased, the average temperature of the hermetic envelope 108 increases. Gravitational convection also increases as does the temperature difference between the bottom and top of the laser tube. As an illustration of the problem, if the average temperature along the top lateral side 1a of the hermetic envelope 1 is greater than the average temperature on the opposite lateral side 1b, the difference in average temperature, dT, creates a differential elongation of the envelope from one side to the other which causes angular rotation of the laser mirrors 100 and 101 relative to the optical axis 5 of the laser tube. The output power of the laser plasma tube is stable when the random thermal deformation angle produced by this average lateral temperature difference, dT, is less than the angular misalignment tolerance of the laser. The misalignment tolerance of a laser plasma tube describes the ability of a laser tube design to withstand angular misalignment of the laser mirrors 100 and 101 before one or more of the laser power, beam position, beam shape, or transverse mode characteristics are degraded to an unacceptable level. The misalignment tolerance depends on the distance between laser mirrors, the diameter of the hollow cathode opening 111, and the radii of curvature of the laser mirrors 100 and 101. Typically the misalignment tolerance of a laser of about 40 cm length is of the order of 50 microradians. Desirable thermal misalignments would be less than 50 microradians. The ratio of the thermal deformation angle divided by the angular misalignment tolerance is defined here as the thermal stability factor (TSF).

The thermal deformation angle, $\theta_D$, of the laser mirrors is proportional to $\alpha(dT)LD$ where $\alpha$ is the thermal expansion coefficient of the hermetic envelope material 108, dT is the average lateral temperature difference between surface 1a and 1b, L is the length of envelope 108, and D is the diameter of 108. The average lateral temperature difference is proportional to P/ktL where P is the input power to the laser, k and t are the thermal conductivity and wall thickness of the envelope 108, respectively. Thus, $\theta_D$ $P(\alpha/k)(1/Dt)$. As typical lasers are scaled to higher power levels, the laser plasma tube is made longer since the optical gain of the tube is typically constant and length is the dominant factor to increase laser output. As lasers are scaled to higher power, the diameter is typically not scaled proportionally. Therefore, as the length is increased, the misalignment angle increases assuming constant input power per unit length. On the other hand, as the length increases, the tolerance angle decreases in inverse proportion to the laser plasma tube length. Combining the proportionality described above, TSF $P(\alpha/k)(L/Dt)$. Laser designs with low values of TSF are more stable while designs with high values of TSF are relatively less stable. The acceptable value of TSF depends on the sensitivity of the application to changes in laser power, mode shape and beam pointing. In the design of a laser plasma tube, the choice of radii of curvature of the laser mirrors 100 and 101, the separation of mirrors, the diameter of the opening 111 (e.g. gain capillary), the length of the opening 111 in the cathode 110 and many other design features of a laser can be used to trade between the efficiency of producing laser output and the sensitivity of the design to thermal instabilities. In general it is always preferred to minimize the value of TSF.

The output wavelength, output power, and mode shape usually determine the hollow cathode (e.g. capillary) length and diameter of the opening 111. Other factors such as the need to protect the mirrors from contamination from the hollow cathode determine the overall length between laser mirrors 100 and 101. The input power is subsequently determined by the length and the diameter of the hermetic envelope 108 and is usually made as small as possible. Other factors such as heat transfer from the hollow cathode 110 and limitations related to desired operating temperature of the hollow cathode also limit the diameter of the hermetic envelope 108. Another choice in the design is the envelope material. It is noted that the equation for thermal stability factor (TSF) contains the ratio of thermal expansion coefficient and thermal conductivity of the hermetic envelope material, $\alpha/k$. This ratio is defined here as the thermal asymmetry coefficient (TAC).

Low thermal expansion and high thermal conductivity are desirable in materials used for the construction of the hermetic plasma tube envelope 108, and end caps 104, and 105. Representative envelope construction materials and their TAC are listed in Table 1.

TABLE 1

TAC for Representative Laser Envelope Materials

| Envelope Material | Thermal Expansion in/in/° C. × $10^{-7}$ | Thermal Conductivity W/in/° C. | Thermal Asymmetry Coefficient in/W × $10^{-7}$ |
|---|---|---|---|
| Beryllia (BeO) | 65 | 5.0 | 13.0 |
| Copper | 169 | 10.0 | 16.9 |
| Beryllium | 116 | 3.5 | 33.1 |
| Invar | 9 | 0.26 | 34.6 |
| Aluminum | 236 | 5.3 | 44.5 |
| 1010 Steel | 126 | 1.3 | 96.9 |
| Kovar (NiFeCo alloy) | 59 | 0.42 | 140.5 |
| Fused Silica | 5.6 | 0.036 | 156 |
| 4750 Alloy (NiFe alloy) | 75 | 0.4 | 187.5 |
| 304 Stainless Steel | 173 | 0.37 | 467.6 |
| 7740 Glass (Pyrex) | 32 | 0.033 | 969.7 |

Clearly beryllia has the lowest thermal asymmetry coefficient of the materials shown. Beryllia also has the desirable property that it is a mechanically stable material with high yield strength. However, it is much more expensive than the other materials listed and is an electrical insulator, which is not convenient in the preferred design described. However, because of its superior TAC, it is expected to be useful for some special applications. Copper also has an excellent thermal asymmetry coefficient. However, it also has low yield strength when annealed and the annealing temperature is very low. Beryllium and Invar have very similar thermal asymmetry coefficients. They are impermeable to the gases of particular interest and can be joined by a wide range of techniques. The choice between these materials is primarily a matter of cost and availability. Aluminum is also a good choice with a relatively low thermal asymmetry coefficient. Aluminum is an especially good material when weight of the laser plasma tube is also of consideration. Materials lower on the list are less desirable because of their rapidly increasing thermal asymmetry coefficient but may be used in some circumstances. The choice of material depends on the laser plasma tube design. For low power lasers (e.g. 500 average watts) with short tube lengths (e.g. 20 inches) the thermal asymmetry coefficient is of less-importance. However, if the mode quality or beam pointing accuracy is of high importance, a low value of thermal asymmetry coefficient is more important. Preferred hermetic envelope construction materials have thermal asymmetry parameters less than about $1\times10^{-4}$, more preferably less than about $200\times10^{-7}$, and most preferably less than about $50\times10^{-7}$.

Further improvement in the stability of these laser plasma tubes can be made by increasing the wall thickness. Typical wall thickness of the laser plasma tube envelope 108 is about 1 to 3 mm, for short laser tubes a smaller wall thickness (e.g. 1 mm) is acceptable. Similarly, for very long laser tubes, a larger wall thickness (e.g. 3–5 mm) is preferred. Another technique to improve stability is by using methods external to the hermetic envelope to suppress unwanted thermal asymmetries with the hermetic envelope 108 such as those taught in references (19) by Hug and (20) by Ekstrand. These external methods include but are not limited to: (1) providing high thermal conductivity solid or liquid materials surrounding and in close proximity to the hermetic envelope to equilibrate temperature differences; and (2) providing air flow in combination with finned heat exchangers to reduce lateral temperature gradients. Liquids such as water, ethylene glycol and the like would be useful for this purpose. Wrapping materials may include aluminum or copper foil that can be used to increase the effective thickness of the hermetic envelope while not being part of the hermetic envelope 108. Operation of the laser plasma tube in a vertical orientation may be used to reduce the average temperature difference between 1$a$ and 1$b$. However, it does not reduce the temperature difference resulting from convective instabilities which may result from air currents around the laser tube that are induced by the temperature difference between the laser plasma tube and the ambient air surrounding the tube.

Referring again to FIG. 1$a$, the laser mirrors 100 and 101 are hermetically sealed or mated to their corresponding adjustment mechanisms 102 and 103. In order to maintain a long shelf and operating lifetime for the laser plasma tube 1, these seals are preferably hermetic and are formed using a non-permeable sealing material or at least a material that is effectively non-permeable (i.e. material passing through the seal is held below a level that would materially impact desired life expectancy of the laser system). By hermetic it is meant that leakage of helium through the seal should be less than about $10^{-7}$ Torr Liter per second though in some circumstances higher leakage may be acceptable. For example, in some cases, the permeability of the hermetic envelope to helium can be perhaps as high as $10^{-4}$ Torr Liter per second. Several methods of sealing are possible which make suitable hermetic seals. However, the sealing method must be compatible with the laser mirror coating, substrate material and mating material. Laser mirror substrate and coating materials vary widely depending of the specific wavelength and whether the mirror is an output coupler 100 or high reflector 101. Therefore, since the lasers disclosed in this patent cover a wide range of wavelengths (e.g. from about 200 nm to 2000 nm), the type of mirror substrate, coating and mating surface can vary substantially. The discussion hereafter will focus primarily on seals that apply to deep UV laser wavelengths in the 200 nm to 300 nm range. Appropriate sealing techniques for the various other wavelength systems contemplated herein will be apparent to those of skill in the art.

The high reflecting laser mirror 101 does not transmit UV laser radiation. Therefore, the substrate material of this mirror can be made from a wide range of materials without regard for its UV transmission, the only criteria being the ability to be adequately polished and coated with appropriate, low loss, laser mirror coatings. Mirror 101 could be made of, for example, Schott BK7 or Schott K5 materials that have been demonstrated to be compatible with polishing and coating with appropriate laser mirror coating materials. The thermal expansion coefficient of these mirror substrate materials is about $84\times10^{-7}/°$ C. Typical materials for the corresponding adjustment mechanism 103 are Carpenter 49 or Carpenter 4750 that have thermal expansion coefficients about $75\times10^{-7}/°C$. It is preferred that the substrate of the mirror has a coefficient of thermal expansion that is within $20\times10^{-7}$ inch per inch per °C. of the coefficient of thermal expansion of envelope material that it is being bonded to. Solder glass or glass frit materials can be used to form an excellent hermetic seal between these glasses and metals at the relatively low sealing temperature of about 500° C. Hermetic compression and brazing may also be used. Of course other hermetic sealing techniques, well known by those of skill in the art, may be used in alternative embodiments.

The output coupling laser mirror 100 must transmit the UV laser wavelengths generated within the laser plasma tube 1. Therefore the bulk material of the laser mirror 100 is typically made of UV transmitting materials such as fused silica or sapphire. Fused silica is very difficult to hermetically seal at low sealing temperatures because of it low thermal expansion coefficient, $5\times10^{-7}/°$ C. Preferred low temperature hermetic seals may be formed with fused silica using a ductile material such as indium, lead, lead/silver or other ductile alloys to form a compression or swag seal wherein the ductile material forms an intimate contact with both the mirror substrate material of mirror 100 and the mating material of adjustment mechanism 102 during the process of extrusion or swaging of the ductile material between mirror 100 and adjustment mechanism 102. Another type of seal is possible when using sapphire as the substrate material for mirror 100. Sapphire has a thermal expansion coefficient of about $65\times10^{-7}/°$ C. Because of the higher thermal expansion coefficient, several mating materials are available to be used in mating to adjustment mechanism 102 which have thermal coefficients within the usual matching range to allow sealing with solder glasses or frits. One possible material for adjustment mechanism 102 is Kovar with a thermal expansion coefficient of $59\times10^{-7}/°$ C. It is preferred that the substrate of the mirror have a coefficient of thermal expansion that is within $20\times10^{-7}$ inch per inch per °C. of the coefficient of thermal expansion of the envelope material that it is being bonded to.

Use of coating materials on the laser mirror surfaces are preferred in the operation of these lasers. These coating may be used to enhance emission at one or more wavelengths and/or to suppress emission at one or more wavelengths. Neon-copper versions of these lasers can emit simultaneously at 248.6 nm, 259.9 nm, 260.0 nm and 270.3 nm. The laser emission lines at 248.6 nm and 270.3 nm share the same upper energy state, and therefore compete for the same population of ions during the lasing process. Therefore the laser output of one of these lines needs to be suppressed if it is desired to optimize the output of the other. If, as an example, the 248.6 nm laser line is to be optimized, the optimum laser output mirror transmission is optimized for the gain and losses of this laser line. For the lasers of the preferred embodiment considered here, this optimum is in the range of 1% transmission. In order to suppress oscillation at the 270.3 nm laser line the transmission of the laser mirror preferably exceeds about 10% in order to ensure that this laser line will not oscillate. In this manner, the laser output at 248.6 nm can be maximized. Helium-silver version of these lasers do not have line competition problems in the deep UV range. However, if silver and copper cathodes are combined in a fashion to provide simultaneous output at 224.3 nm from the silver and 248.6 nm from the copper, it would be desirable to provide a laser mirror which optimizes the oscillation at 224.3 nm and 248.6 nm and suppresses oscillation at 270.3 nm.

Referring again to FIGS. 1a and 1b, the interior surface of the hollow cathode 110 that at least partially surrounds opening 111 is the source of metal ions that provide the gain material for lasing. The hollow cathode in the case illustrated in FIGS. 1a and 1b is a metal capillary tube with a slot along one side facing the anode. The entire hollow cathode 110 or only the inner surface may be made of the optically active material of interest (e.g. copper, silver or gold). The slot extends over the entire length of the capillary tube in the case shown. Exact dimensions of the optimum slot length, width, and height depend, inter alia, on the particular laser material employed. For a given cathode material optimal or acceptable parameters may be derived empirically. In a preferred embodiment using a copper cathode the opening has a circular cross-sectional shape with a diameter in the range of 2–5 mm, a cathode length of 100–400 mm, a slot width in the range of 1–3 mm, and a slot height of 0.5–2.0 mm, and a slot length similar to the cathode length. The cathode capillary is suspended in a buffer gas that fills the interior of the cathode (i.e. opening 111). Upon application of a sufficient potential between anode 112 and cathode 110, the opening 111 of the cathode fills with a gas discharge. The hollow cathode discharge is a relatively field-free negative-glow discharge mostly filling the interior region of the hollow cathode except for a thin sheath that hugs the interior walls of the cathode. The space potential of the negative-glow discharge is nearly equal to the anode potential. The voltage drop across the sheath is therefore nearly equal to the full anode-cathode voltage which typically ranges from about 250V to about 500V for the cathode materials of particular interest in the preferred embodiments. Of course other voltage ranges are possible. Electrons leaving the interior surface of the cathode are accelerated in the sheath region adjacent to the cathode surface to energies dictated by the cathode fall potential. These energetic electrons lose their energy in ionizing and excitation collisions with the buffer gas atoms. The inside diameter of the cathode capillary (i.e. the diameter of the opening 111) is small enough (preferably between 2–5 mm, more preferably between 2–4 mm) so that, with desired buffer gas pressures (e.g. preferably between 2 and 30 Torr of helium or neon, and more preferably between 5–20 Torr) and voltage levels (e.g. between 250–500 volts), the electron beam created in the sheath at the inner surface of the cathode, has a reaching distance longer than the inner diameter of the capillary.

The opening 111 does not need to be circular and can, in general, be of any desired geometry. However, since the desired laser beams are normally circular, and because of the ease of producing circular openings, a circular cathode opening 111 is typical. The electrons will oscillate between opposing walls inside the cathode. Buffer gas ions are accelerated back through the sheath and bombard the cathode surface, causing sputtering of the metal atoms of the cathode inside surface material. As the discharge fully develops the source of electrons is dominated by secondary electron emission due to bombardment of the cathode interior surface by buffer gas and metal ions, metastable atoms, and photons. The cause of metal atoms ejected from the cathode wall is bombardment by buffer gas and metal ions and metastable atoms within the negative glow in the opening 111 in the hollow cathode.

The optical gain of the laser depends on the population density of metal ions in the upper and lower excited states for the desired transition which, in turn, depends on the metal atom density, charge-transfer excitation rates, and geometry. In hollow cathodes of the type described here, the metal atom density and excitation rates are coupled together in the sputtering process. Thus, in a given cathode geometry, if the density and excitation rates are not simultaneously optimum, a preferred method of optimizing the optical gain is to vary the geometric shape of the cathode.

Figure 2A:
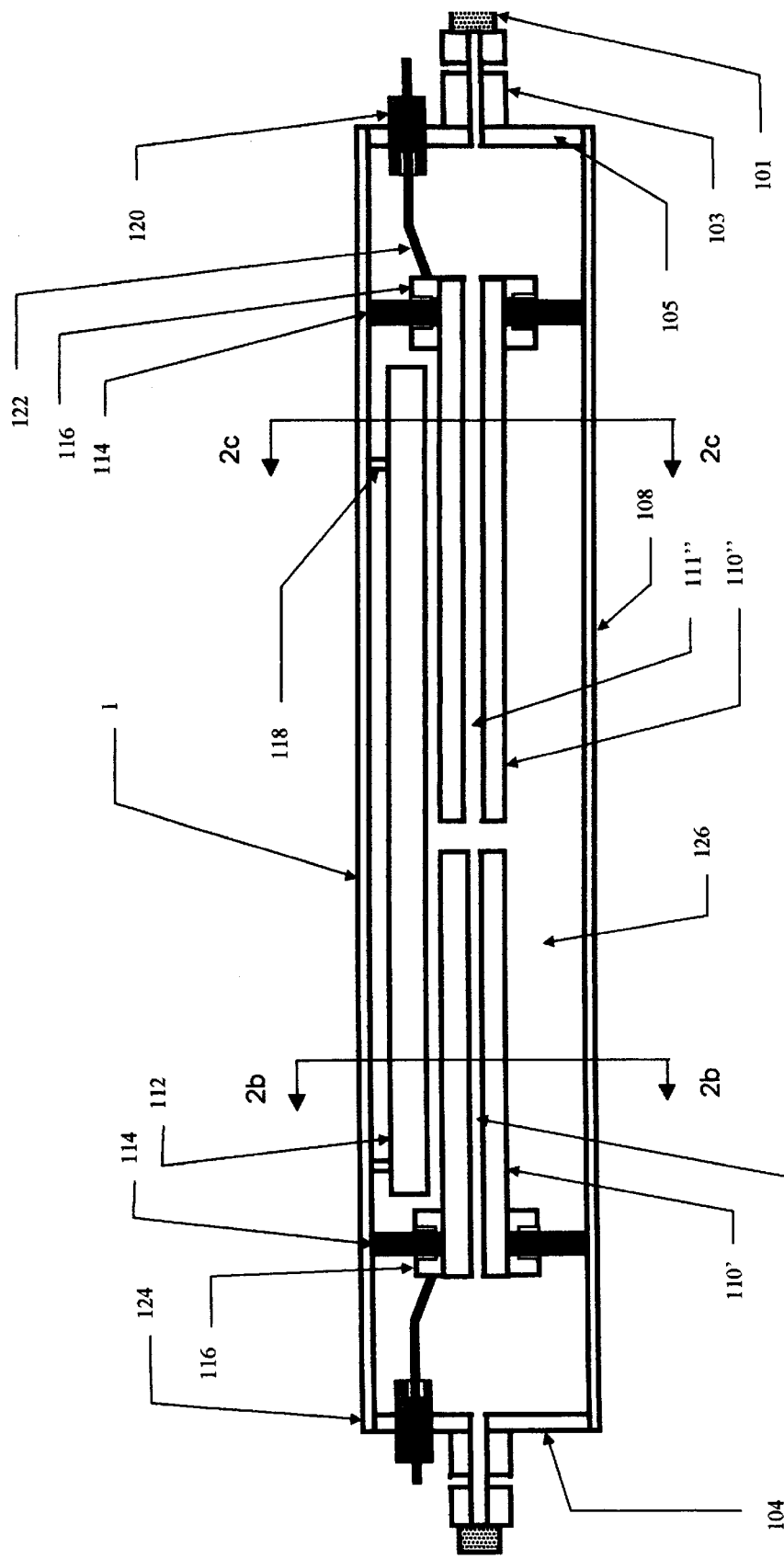
FIG. 2a depicts a longitudinal cross-sectional view of a multi-metal internal mirror/internal resonator hollow cathode sputtering metal ion laser.
Figure 2B:
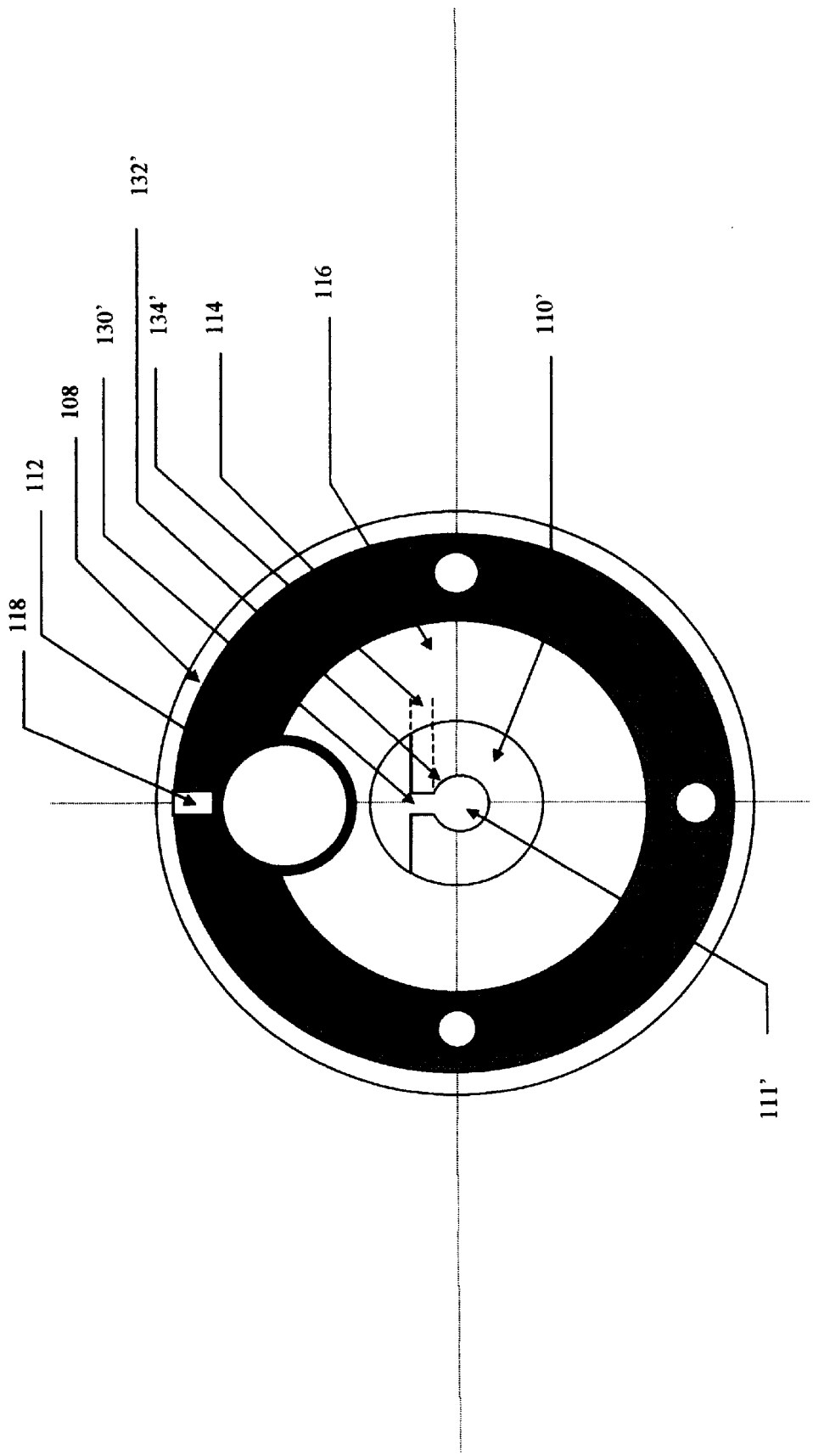
FIG. 2b depicts a cross-sectional view of the laser of FIG. 2a along lines 2b—2b.
Figure 2C:
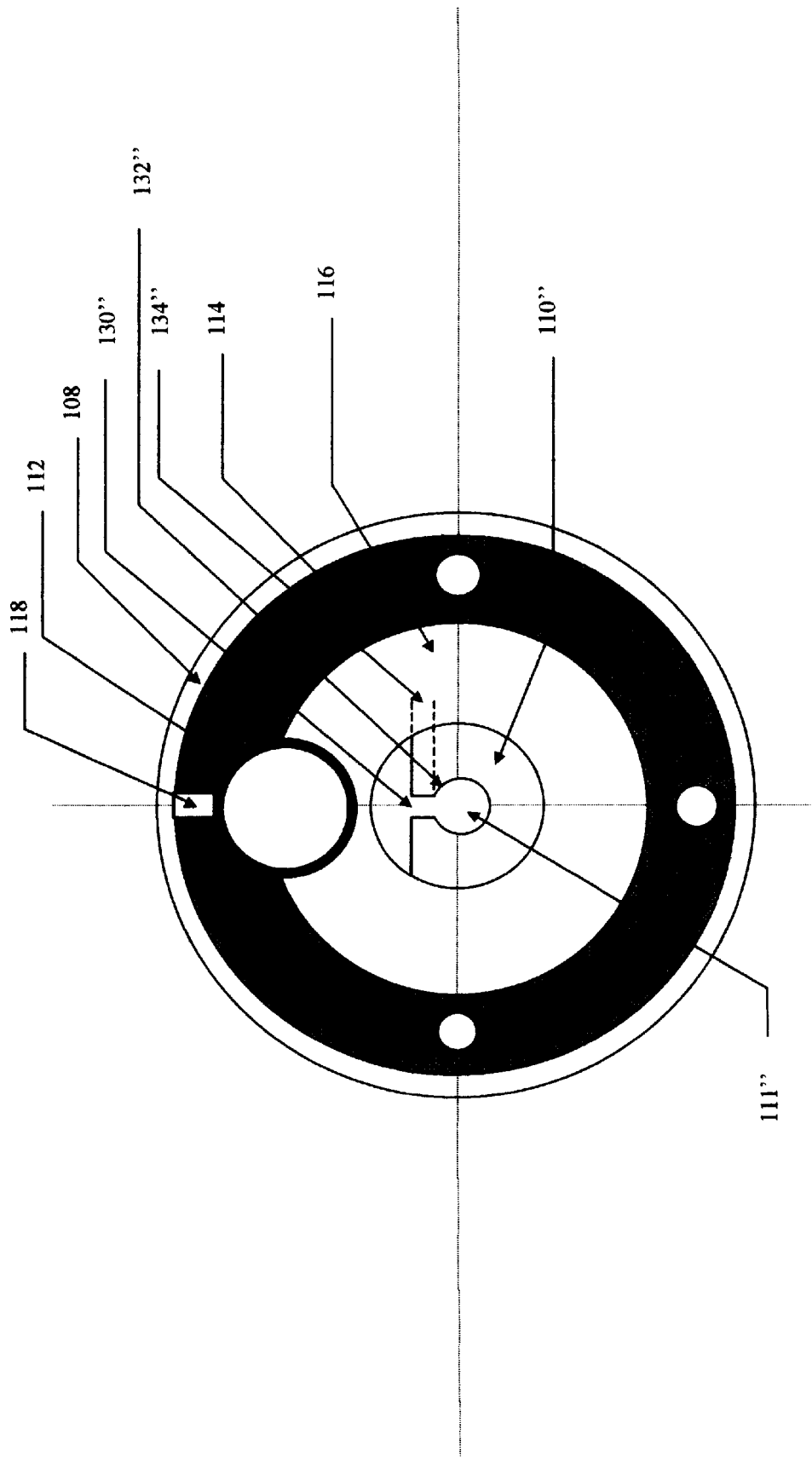
FIG. 2c depicts a cross-sectional view of the laser of FIG. 2a along lines 2c—2c.

Referring to FIGS. 2a, 2b, and 2c two or more cathodes of different metals 110' and 110" can be used within the same hermetic laser plasma tube envelope 1 to provide simultaneous output at one or more laser emission lines characteristic of each metal. The performance of each cathode 110' and 110" can be separately optimized using geometric variations, such as inside diameters 132' and 132" of the openings 111' and 111", slot widths 130' and 130", slot heights 134' and 134", and also by varying buffer-gas fill-pressure, gas mixture and combinations of these parameters. In addition, each cathode can be powered by the same or a separate power supply to provide emission either in-phase or out-of-phase with the emission of another cathode. This provides a large level of flexibility in adapting the laser to a variety of applications.

Other configurations and methods of optimization that utilize multiple metal hollow cathodes to provide multiple laser emission wavelengths are also possible. As an example, a cathode may employ two metals, or more, within the same cathode as longitudinally segmented or radially segmented strips. Alternatively, two cathodes of different materials could be in separate chambers of the laser plasma tube, separated by a Brewster angle window, so that the buffer gas type and fill pressure can be optimized separately for the different cathode materials.

A specific problem associated with hollow cathode sputtering metal ion lasers is the formation of arcs within the laser tube. When an arc is formed within a hollow cathode sputtering metal ion laser several deleterious effects may occur: (1) laser output ceases during the arc, (2) cathode material is blown off the surface and can contaminate laser mirrors or other optical surfaces, or (3) shorts can occur internal to the laser plasma tube which may end the life of the tube.

Preferred cathode materials include silver, copper, and gold. The copper may be used to supply, inter alia, one or more of 248, 260, and 270 nm radiation and other emission wavelengths. The gold may be used to supply, inter alia, one or more of 282, 285, 289, and 292 nm radiation and other emission wavelengths. The silver may be used to supply, inter alia, one or more of 224 nm radiation and other emission wavelengths. Particularly preferred combinations of metals for cathodes include copper and gold, copper and silver, and silver and gold. Of course, use of other metals and other combinations of metals are possible.

Normally during the application of a voltage between anode and cathode, a relatively uniform glow discharge plasma is created within the hollow cathode. If for any reason there exists a small region of the cathode which feeds electrons at an abnormally high rate into the plasma, electromagnetic fields can be created by such currents which cause the normally uniform plasma to collapse into a small thread of ions and electrons called an "arc". This condition can occur because of several phenomena: (1) the formation of a field emission point on the cathode, (2) by heating of the cathode locally to the point of thermionic emission, (3) by an abrupt release of trapped gas in a pocket within the cathode, or (4) by local catastrophic breakdown of the cathode material due to electric forces. This last phenomenon may occur if an insulating area exists or occurs on the cathode surface due to oxidation of the cathode by contaminants within the laser. If this occurs, the insulating area is charged by bombarding ions until the voltage difference across the insulator builds up to a point where the insulator breaks down in a sudden catastrophic event.

An arc is characterized by a much lower voltage drop than the usual glow discharge: less than 100V(and often less than 20V) compared to 250V to 500V for the glow discharge. Because of the resulting abrupt drop in impedance, the arc will often "dump" the energy stored in the plasma and in the output of the power supply used to create the dc cathode potential. If the stored energy in the output stage of the power supply is too large, the intense power density at the cathode results in melting locally of the cathode and forcible ejection of a substantial amount of cathode material.

To alleviate the potential of arcing within the laser tube several things can be done alone or in combination. First, at least one or more parts within the interior of the laser plasma tube which operate at cathode potential are preferably not allowed to be in contact with an insulating material unless the contact region is provided with an overhang geometry. Appropriate overhang geometries typically depend on buffer gas pressure. The purpose of these overhangs is to ensure that the direct contact point between a conductor at the cathode potential and supporting insulators cannot be charged up due to ion bombardment. Most preferably all parts, within the laser cavity, operating at the cathode potential, are not allowed to contact insulating material unless an overhanging geometry is used. It should be appreciated that certain parts and circumstances may allow contacts without overhang geometries to be used.

FIGS. 3a, 3b, and 3c depict several preferred embodiments for implementing overhanging geometries for establishing a connection and/or support between the anode and a conductor at the cathode potential $P_c$ 110 within the laser plasma tube. As noted above the reduction in arcing that can result from use of overhanging geometries may significantly enhance operation and lifetime of the laser. The anode and cathode of hollow cathode sputtering metal ion lasers are operated with a potential difference typically between 200V and 500V for most cathode materials. This voltage is determined primarily by the atomic properties of the cathode inner surface material and buffer gas. A buffer gas 126 is employed to initiate electrical breakdown between anode and cathode, to initiate sputtering and provide excitation. Preferred buffer gases are typically noble gases. These gases may be used singly or in mixtures. These gas may include radioisotopes. In the preferred laser embodiments of this patent the buffer gas pressures are typically between 3 Torr and 40 Torr. Separating the anode and cathode by a dielectric material 114 so that the electrodes are not shorted together. Direct contact between electrical conductors at the cathode potential and insulating materials used to separate and/or support the anode and cathode are preferably designed in a manner that avoids arcing and thus shortened lifetime of these devices and unreliable operation.

FIG. 3a depicts contact between a dielectric 114 (i.e. insulating material) and a conducting surface at the cathode potential $P_c$ where an undercut is provided in the insulating material.

FIG. 3b depicts contact between a dielectric 114 (i.e. insulating material) and a conducting surface at the cathode potential $P_c$ where an undercut is provided in the conducting material at the cathode potential $P_c$.

FIG. 3c depicts contact between a dielectric 114 (i.e. insulating material) and a conducting surface at the cathode potential $P_c$ where an undercut is provided by sandwiching the dielectric between supplemental conducting elements 116 which are at the cathode potential $P_c$.

Referring to FIGS. 3a, 3b, and 3c, it has been found that the optimal gap, d, between electrically conducting materials at the cathode potential $P_c$ and the surface of the dielectric material depends on the pressure, p, of the buffer gas. It has been found that the product of the buffer gas pressure, p, and the separation distance, d, preferably have values between 0.1 Torr mm and 3.0 Torr mm. As values move toward the limits of this range and beyond the likelihood of arc formation and excessive sputtering and erosion at the junction of the electrical conductor at cathode potential and the dielectric support increases. It has also been found that the depth of the overhang, L, is preferably greater than three times the separation distance d (i.e. 3d) and more preferably greater than five times the separation distance d (i.e. 5d) and most preferably greater than ten times the separation distance d (i.e. 10d). Separation distance and depth of overhang in these ranges helps ensure that a sufficiently large potential difference cannot be created at the juncture of cathode and insulator materials to cause the formation of catastrophic breakdown, or arc. Though preferred gaps have a constant separation width, d, it should be appreciated that other embodiments are possible where the separation width, d, is not constant along the length of the overhang.

Another method of arc reduction is to limit the energy stored in the output stage of the power supply. If the energy stored between the final switching device in the power supply and the laser plasma tube is sufficiently small, formation of an arc can be sensed in time to stop the discharge from collapsing into a damaging arc.

A further method of arc reduction is to operate the hollow cathode sputtering metal ion laser in a duty cycled or commutated mode. Depending on how it is implemented, this may provide for two arc reduction features: First, reduction of localized heating and associated reduction of the potential to achieve local thermionic emission within the hollow cathode, thereby reducing chances of producing an arc, and second by allowing for frequent and periodic reversals of the operating voltage on the cathode to discharge any surface charge built up on insulating layers on the cathode. By operating the hollow cathode sputtering metal ion laser with pulse widths from a few tens of microseconds to about one millisecond there is inadequate time for gross thermal non-uniformities to occur within the cathode to produce arcing. And with these short pulse widths the opportunity exists to reverse the voltage of the cathode at the end of each pulse, for example to a value about one-tenth of the operating cathode voltage for a period of between 10 and 100 microseconds, to discharge any charge buildup on insulating materials on the cathode surface.

Laser output continues at all emission lines of the hollow cathode metal ion lasers as long as input power above threshold is applied. The laser emission process is thus continuous and the output is described as CW or continuous wave. As described previously, the input power required to reach laser threshold varies from laser line to laser line. However, the range of input power levels ranges from about 500W to over 5000W depending on the specific laser line of interest. The size, weight, and cost of laser plasma tubes, cooling systems and power supplies is nominally proportional to average power. Therefore it is desirable to operate the laser in such a manner that the input power is commutated or pulsed such that, during a pulse the input power is above laser threshold for the desired laser lines and the average power is below threshold. Thus the laser tube and power supply designs can be scaled for the low average power, thereby reducing the overall cost and complexity of the laser system.

It is preferred that the instantaneous power of the system be greater than 1000 watts and the average power be under 500 watts. It is more preferred that the instantaneous power is greater than 5000 watts and the average power is less than 200 watts. Preferred pulse widths are less 1000 microseconds, more preferred pulse widths are less than 500 microseconds and most preferred pulse widths are less than 300 microseconds.

During a discharge current pulse the input power is above a value needed to reach threshold for emission at the desired laser emission line. Typically laser output occurs within 10 to 20 microseconds after application of discharge current. No simmer or keep-alive voltage or power is needed to keep the laser warm. The laser can be operated without preheating over a wide range of ambient temperatures. The voltage and power capability of the power source can be very low and depend only on the short term and long term duty cycle needed to support the average laser output requirements of a particular application. The laser can be operated in a manner very much like a flashlamp or strobe lamp. The laser can provide a single pulse, bursts of pulses or continuous pulses at a wide range of short term average and long term average input power.

Figure 4A:
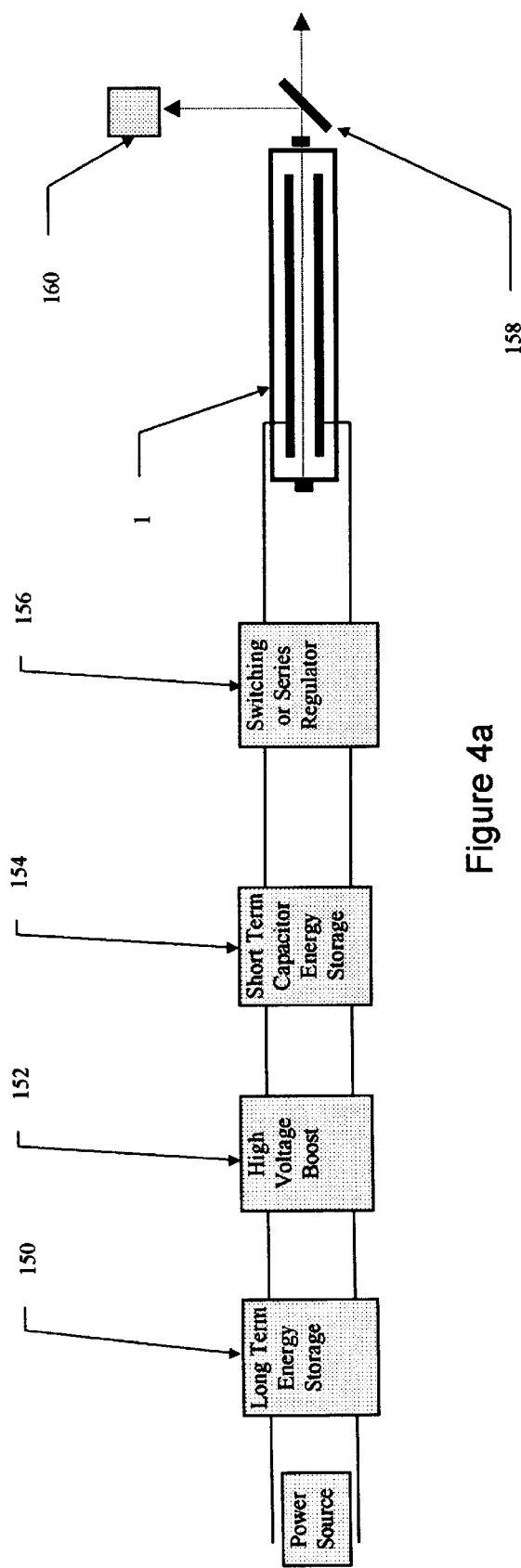
FIG. 4a depicts a block diagram of the power conversion electronics of a preferred power supply for driving the laser.

FIG. 4a shows a block diagram of preferred power conditioning electronics useful to operate the sputtering metal ion hollow cathode laser discussed above in association with FIGS. 1a and 1b. The figure shows an external source of power 148 to operate the laser, a device 150 for storing energy (preferably in an efficient and compact manner), a device or circuit 152 for efficiently boosting the voltage to a voltage equal to or higher than is required of the laser plasma tube (preferably greater than 500VDC), a capacitor or other device 154 for filtering and storing energy at the higher voltage, a regulating device 156 to provide a desired pulse pattern (e.g. relatively square-wave input pulses) to the laser plasma tube 1. This pulse pattern may be applied in either an open-loop or closed loop fashion. A closed loop system may use one or more of voltage detection, current detection or optical feedback. Optical feedback may be obtained by using a beam splitter 158 or other detection device and detector 160 to regulate the output power of the laser.

Examples of the external source of power 148 are normal alternating line voltage provided by a power company, a battery or solar panel. Examples of the primary energy storage device 150 within the laser power supply would be a battery or capacitor, depending of the operating usage defined for the laser. As an example, if the laser were to be operated in bursts, such that the long term average laser power available to the laser was very low (less than 10W, as an example) and the short term average operating power of the laser was high (greater than one hundred watts, as an example), the primary energy storage device 150 would preferably be a battery which has very high energy density storage. If the usage rate were steadier, 150 would preferably be a capacitor.

The higher voltage or voltage stored in capacitor 154 must be sufficient to breakdown the buffer gas between the anode and cathode and form a hollow cathode discharge. For neon-copper lasers this voltage is typically about 400 VDC. For helium-silver lasers this voltage is typically about 600 VDC. The energy stored in this capacitor is typically several times greater than the energy dumped into the laser in a single pulse. Typically the energy input to the laser plasma tube per pulse is less than 10J. Therefore the energy stored in capacitor 154 would be of the order of 50J to 100J.

The switching device 156 can be as simple a single transistor or a more complicated circuit to compensate for impedance variances during formation of the discharge within the laser plasma tube.

Some preferred features of this power supply are that it be designed with very low stored energy in the final output stage of the switching circuit that supplies power to the laser plasma tube and/or that the pulse regulating device provide voltage reversal at the end of each pulse (or periodic pulses) of between about 2% and about 10% of normal operating voltage. As discussed above, a purpose in limiting the stored energy in the output stage to the laser plasma tube and/or the voltage reversal is to reduce arcing within the plasma tube. When an arc begins to form within the laser tube, the voltage between anode and cathode begins to drop rapidly. As an example, the normal voltage waveform for a neon-copper version of this laser rises from zero (or near zero) to a voltage about 350V to 400V at the leading edge of a pulse. As the metal ion density develops within the opening 111 of the hollow cathode, the voltage drops to about 250V. The voltage remains steady near 250V for the duration of the pulse until the pulse is terminated, after which the voltage again returns to near zero. If an arc begins to form between anode and cathode, the voltage will drop to less than 100V and usually less than 50V in a short period of time, typically less than 10 microseconds. When an arc begins to form, the negative glow discharge within the hollow cathode is disrupted and all of the energy begins to flow into the arc, which is a localized area of breakdown between anode and cathode. Laser output ceases when the arc forms. In addition, damage can be done to the cathode if this process is allowed to go on for extended periods, perhaps 1 hour or less.

In preferred embodiments, the energy stored in the circuitry between the switching device 156 and the laser tube is sufficiently small that the switching device can terminate the pulse before a damaging arc forms. If too much energy were stored, a large arc could be formed which would damage the laser before the switching device could stop the electric current. A typical limit to the amount of energy stored in the circuit between the switching device and the laser plasma tube would preferably be less than that associated with a capacitance of about 10 microfarads, more preferably less than 1 microfarad, and most preferably less than 0.1 microfarads. If the output capacitance is sufficiently low, a circuit or other device could be used to sense a sudden voltage drop between anode and cathode and could trigger termination of the pulse before damage is done.

Figure 4B:
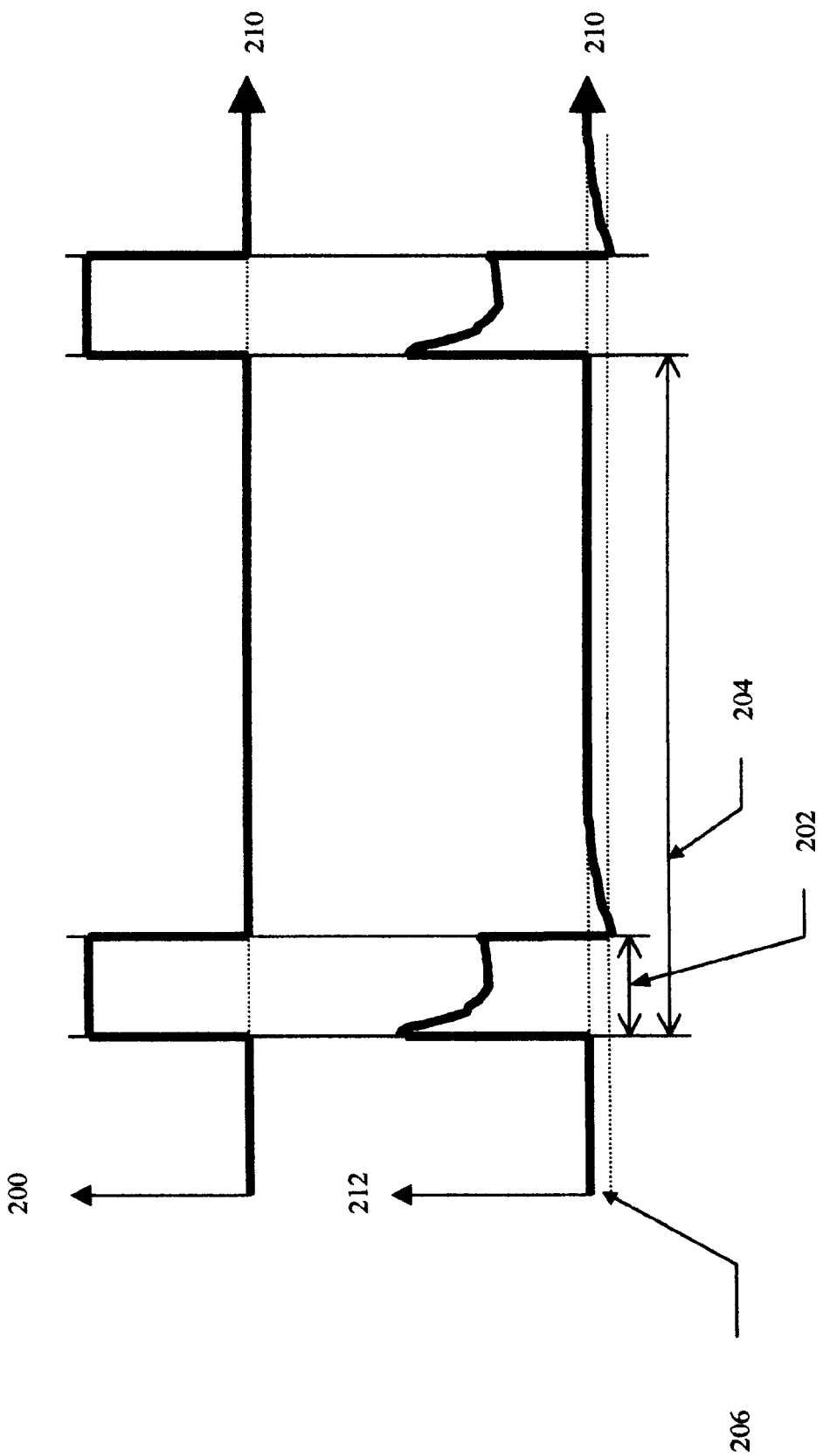
FIG. 4b depicts an example of laser voltage and current pulse waveforms.

FIG. 4b depicts an example of the current input and potential difference between the cathode and the anode during a full cycle. The upper portion of FIG. 4b depicts a plot of current 200 versus time 210 while the lower portion of FIG. 4b depicts a plot of voltage 212 versus time 210. In this example a square wave current is supplied having a pulse width 202 and a period 204 between pulses equal to the reciprocal of a pulse rate frequency. As indicated, for each pulse, the voltage between the anode and cathode is high when the current is first supplied and thereafter reduces to a value that sustains the glow discharge. As can be seen after the current pulse ends the voltage across the anode and cathode is reversed for a period of time. During reversal the applied reverse voltage 206 is an effective amount to discharge build up of charge on dielectric surface. In some preferred embodiments the reverse voltage is greater than about 2% of the maximum voltage used and less than an amount that would result in reverse breakdown.

EXAMPLE APPLICATIONS

A large commercial opportunity for analytical instruments can be enabled by a laser that has the size, power consumption, complexity and cost of a HeNe laser or deuterium lamp system while providing the desired deep UV emission wavelengths with continuous or nearly continuous emission. For example in nearly continuous emission, the duty cycle (ratio of peak power to average power or ratio of pulse period to total period) is preferably greater $10^{-4}$, more preferably greater than $10^{-3}$, and most preferably greater than $10^{-2}$.

Analytical instruments in the context of the present application refer to instruments that analyze a sample of material by exposing that material to a radiation and then detecting selected radiation resulting from the interaction between the incident radiation and the sample. Preferred systems would also include a computer and appropriate software to aid in the analysis. Sample analytical instruments include Raman spectroscopy systems, UV resonance Raman spectroscopy systems, electrophoresis systems (e.g. gel plane or capillary type), and high performance liquid chromatography systems. The samples to be analyzed may be labeled or non-labeled. The samples may be of DNA or molecular or chemical structures.

Figure 5:
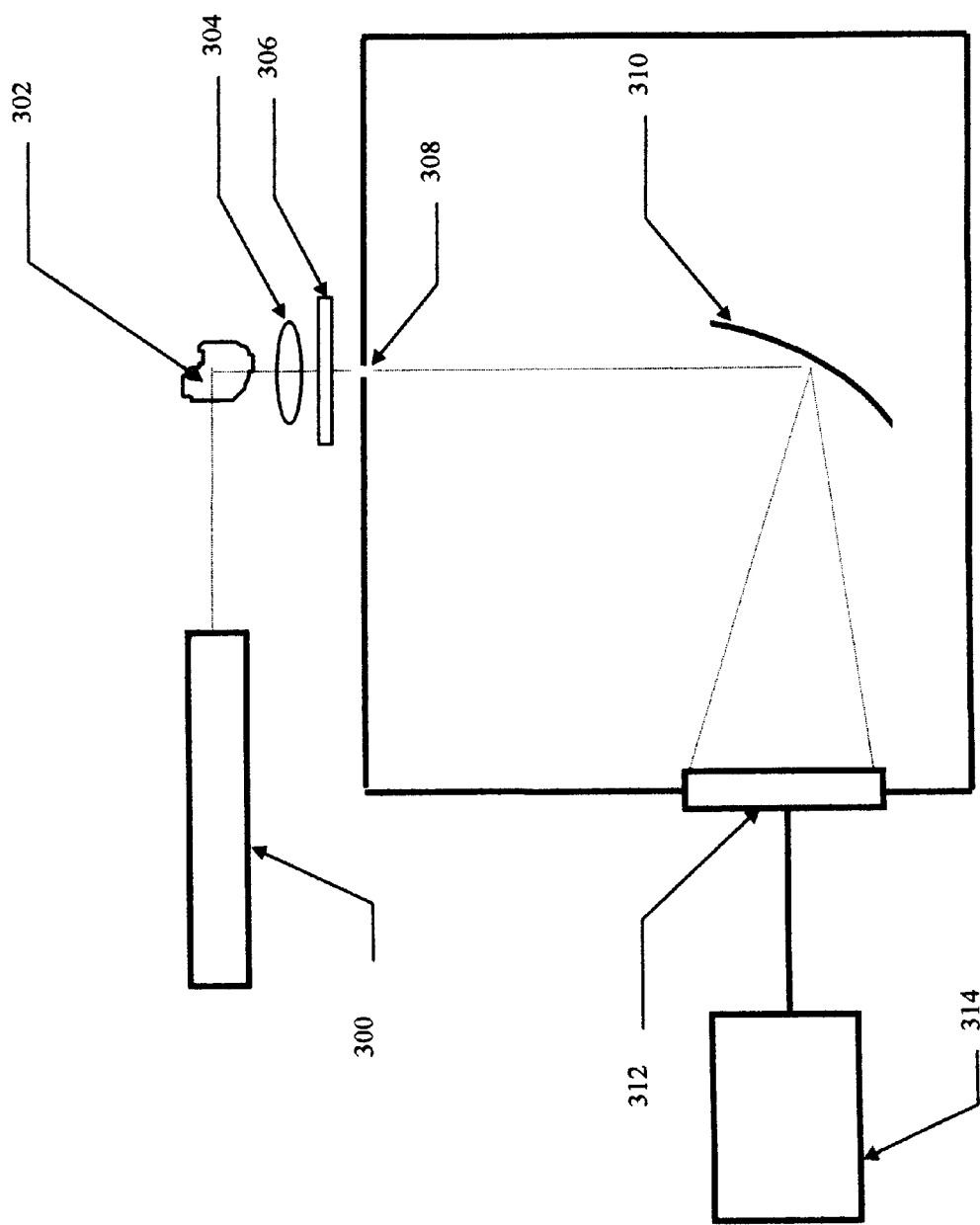
FIG. 5 depicts a schematic representation of a Raman spectroscopy instrument using a hollow cathode sputtering metal ion laser as a light source.

FIG. 5 illustrates the elements of a Raman spectroscopic system. A laser output beam from a sputtering metal ion hollow cathode laser 300 is incident on a sample of material 302 to be analyzed. The Raman emission from the sample is collected with optics 304, passed through an edge filter 306 which is used to block scattered light at the laser emission wavelength and focused onto the entrance slits 308 of a monochromator within which is a wavelength dispersive grating element 310 and a CCD array detector 312. The output data from the CCD array are processed by computer 314. An alternative to the CCD array detector would be the use of traditional exit slits, a detector, and a method of rotating the grating or other dispersion device to scan the dispersed light across the exit slits. The monochromator/spectrometer can be a single device as shown, or a multiple-monochromator device, commonly used for higher resolution requirements.

Figure 6:
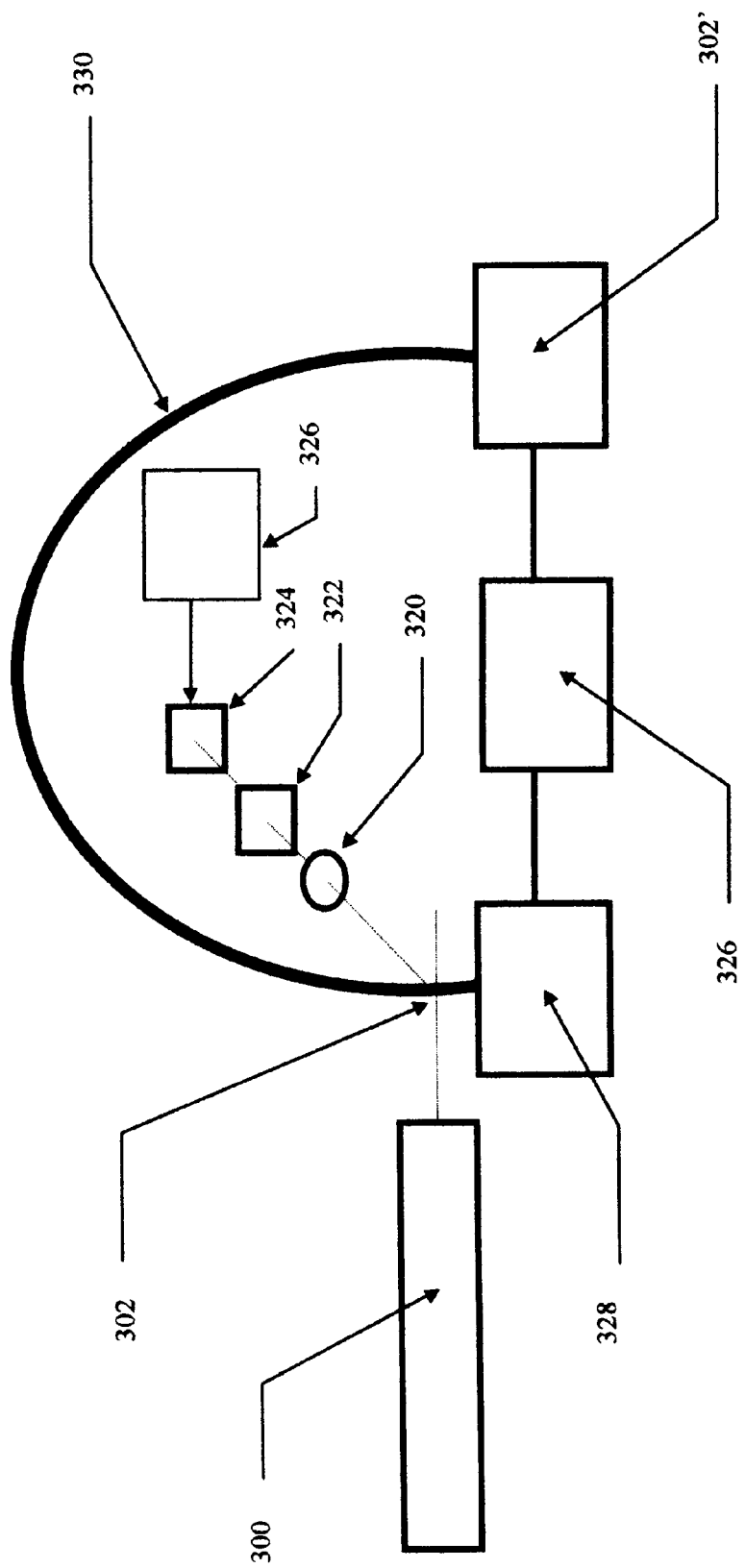
FIG. 6 depicts a schematic representation of a possible capillary electrophoresis instrument using a hollow cathode sputtering metal ion laser as a light source.

FIG. 6 illustrates the elements of a capillary electrophoresis instrument with a laser induced fluorescence detector. A laser output beam from a sputtering metal ion hollow cathode laser 300 is incident on a sample of material 302 inside capillary 330. The sample of material has been separated or segregated from a sample source 302' by the process of electrophoresis and dumped into reservoir 328. Power supply 318 provides the high voltage, low current needed to drive the electrophoretic separation process. The separated material 302 fluoresces when excited by the laser due to absorption by natural or labeling fluorophors within the sample. The fluorescence light is collected by lens 320, passed through filter 322 which blocks Raleigh scattered light at the laser wavelength, and is collected by detector 324 and processed by computer 326. Variations of this optical detection method might use a sputtering metal ion hollow cathode laser in conjunction with a refractive index detector or Raman spectroscopic detector. The electrophoretic separation can be done in a capillary, as illustrated in FIG. 6 or in a planar gel, which is in common use. The system may also include one or more wavelength blocking elements for separating one or more bands of fluorescence emission wavelengths excited in a sample by the incident radiation.

Figure 7:
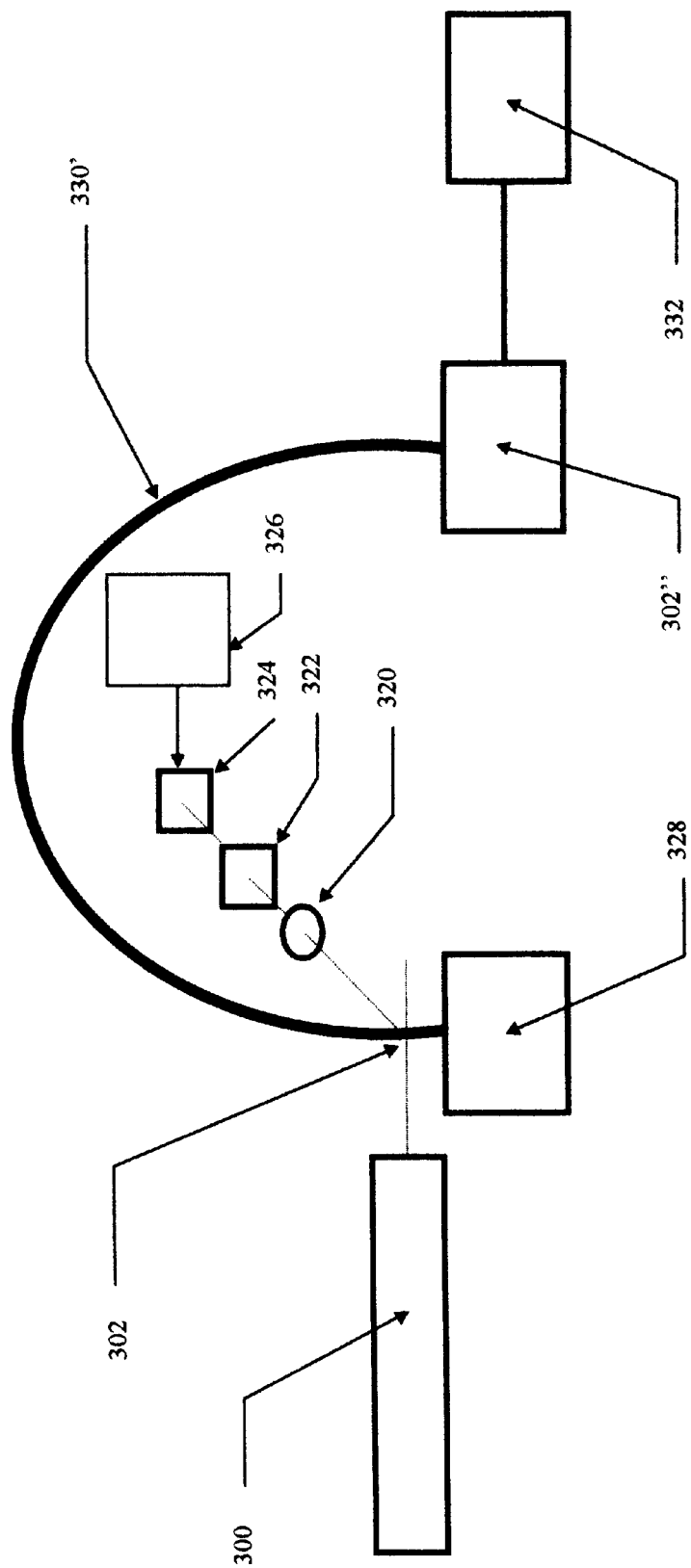
FIG. 7 depicts a schematic representation of a liquid chromatography instrument using a hollow cathode sputtering metal ion laser as a light source.

FIG. 7 illustrates the elements of a liquid chromatography instrument with a laser induced fluorescence detector. A laser output beam from a sputtering metal ion hollow cathode laser 300 is incident on a sample of material 302 within capillary 330' which has been separated or segregated from a sample source 302" by the process of liquid chromatography and dumped into reservoir 328. The separation process is driven by pressure supplied by pump 332. The separated material 302 fluoresces when excited by the laser due to absorption in natural or labeling fluorophors within the sample. The fluorescence light is collected by lens 320, passed through filter 322 which blocks Raleigh scattered light at the laser wavelength, is collected by detector 324 and processed by computer 326. Other variations of this optical detection method may use a sputtering metal ion hollow cathode laser in conjunction with a refractive index detector or Raman spectroscopic detector. Further details about various analytical instruments are provided in the references (1) through (12) as previously discussed and incorporated by reference.

The use of sputtering metal ion hollow cathode lasers in the above applications greatly simplifies these types of instruments by providing one or more of, and most preferably all of, the following enhancements: deep ultraviolet radiation, new probing wavelengths, selectable wavelengths, and reasonable peak power, average power, pulse rate and pulse width all from a compact, light weight laser which has low power consumption.

FURTHER ALTERNATIVES

Other alternative embodiments and uses of the lasers of the instant invention are possible. For example, though the instant invention has been described primarily in terms of efficient and compact deep UV laser systems, larger, higher powered, longer wavelength UV, visible, and even IR radiation producing systems are possible.

In view of the teachings herein, many further embodiments, alternatives in design and uses of the instant invention will be apparent to those of skill in the art. As such it is not intended that the invention be limited to the particular illustrative embodiments, alternatives and uses described above but instead that it be solely limited the by claims presented hereafter.

We claim:

1. An analytical instrument, comprising:
   a. a holder for holding a sample to be analyzed;
   b. a source of radiation producing a narrow band of wavelengths, comprising:
      i. a hollow cathode having an inner surface at least partially surrounding an opening;
      ii. an anode spaced from the cathode;
      iii. a hermetic envelope enclosing a buffer gas and the opening;
      iv. a first mirror having a high reflective surface, wherein the high reflective surface is at least partially within the hermetic envelope;
      v. a second mirror having a partially transmitting surface, wherein the partially transmitting surface is at least partially within the hermetic envelope;
      vi. an optical axis defined by the first mirror and second mirror and extending through the opening; and vii. a source of electric power connected to the anode and cathode forming an optical gain medium within the opening;
c. at least one element for causing the radiation to be incident on the sample; and
d. a detection system for detecting selected radiation resulting from interaction between the incident radiation and the sample.

2. The system of claim 1 wherein the detection system comprises a wavelength dispersive element for separating the radiation resulting from the interaction.

3. The system of claim 2 wherein the analytical instrument is a Raman spectroscopy system.

4. The system of claim 3 wherein the Raman spectroscopy system comprises a UV resonance Raman spectroscopy system.

5. The system of claim 1 wherein the detection system comprises a wavelength blocking element for separating one or more bands of fluorescence emission wavelengths excited in a sample by the incident radiation.

6. The system of claim 5 wherein the analytical instrument is an electrophoresis system.

7. The system of claim 6 wherein the electrophoresis system is a capillary or gel plane system.

8. The system of claim 5 wherein the sample is non-labeled.

9. The system of claim 5 wherein the sample is labeled.

10. The system of claim 5 wherein the sample is DNA.

11. The system of claim 1 wherein the analytical instrument is a high performance liquid chromatography system.

12. The system of claim 9 wherein the sample is non-labeled.

13. The system of claim 9 wherein the sample is labeled.

14. A sputtering metal ion hollow cathode laser system for use in an analytic instrument that analyzes chemical composition or structure of a sample, comprising:
a hollow cathode having an inner surface at least partially surrounding an opening;
an anode spaced from the cathode;
a hermetic envelope enclosing a buffer gas and the opening;
a first mirror having a high reflective surface, wherein the high reflective surface is at least partially within the hermetic envelope;
a second mirror having a partially transmitting surface, wherein the partially transmitting surface is at least partially within the hermetic envelope;
an optical axis defined by the first mirror and second mirror and extending through the opening; and
a source of electric potential connected to the anode and cathode for forming an optical gain medium within the opening, wherein a beam of laser radiation is produced and said beam is used in the analytic instrument.

15. The system of claim 14 wherein the analytical instrument comprises a wavelength dispersive element for separating the radiation resulting from interaction.

16. The system of claim 15 wherein the analytical instrument is a Raman spectroscopy system.

17. The system of claim 16 wherein the Raman spectroscopy system comprises a UV resonance Raman spectroscopy system.

18. The system of claim 14 wherein the analytic instrument comprises a wavelength blocking element for separating one or more bands of fluorescence emission wavelengths excited in a sample by the radiation.

19. The system of claim 18 wherein the analytical instrument is an electrophoresis system.

20. The system of claim 19 wherein the electrophoresis system is a capillary or gel plane system.

21. The system of claim 20 wherein the sample is non-labeled.

22. The system of claim 20 wherein the sample is labeled.

23. The system of claim 20 wherein the sample is DNA.

24. The system of claim 14 wherein the analytical instrument is a high performance liquid chromatography system.

25. The system of claim 24 wherein the sample is non-labeled.

26. The system of claim 24 wherein the sample is labeled.

27. A method of analyzing the chemical structure of sample, comprising:
a. holding a sample to be analyzed;
b. producing a narrow band of wavelengths of radiation, comprising:
i. providing a hollow cathode having an inner surface at least partially surrounding an opening;
ii. providing an anode spaced from the cathode;
iii. providing a hermetic envelope enclosing a buffer gas and the opening;
iv. providing a first mirror having a high reflective surface, wherein the high reflective surface is at least partially within the hermetic envelope;
v. providing a second mirror having a partially transmitting surface, wherein the partially transmitting surface is at least partially within the hermetic envelope;
vi. relatively positioning the first mirror, the second mirror, and the opening to form an optical axis defined by the first mirror and second mirror and extending through the opening; and
vii. providing a source of electric power connected to the anode and cathode to form an optical gain medium within the opening, wherein a narrow band of wavelengths is produced;
c. causing the radiation to be incident on the sample; and
d. detecting and analyzing selected radiation resulting from interaction between the incident radiation and the sample, such that chemical analysis of the chemical structure is achieved.

* * * * *